(12) United States Patent
Splett et al.

(10) Patent No.: US 12,714,321 B2
(45) Date of Patent: Aug. 25, 2026

(54) METHOD AND APPARATUS FOR DETERMINING HEART RATE

(71) Applicant: Medtronic, Inc., Minneapolis, MN (US)

(72) Inventors: Vincent E. Splett, Apple Valley, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 679 days.

(21) Appl. No.: 18/159,064

(22) Filed: Jan. 24, 2023

(65) Prior Publication Data

US 2023/0263416 A1 Aug. 24, 2023

Related U.S. Application Data

(60) Provisional application No. 63/312,367, filed on Feb. 21, 2022.

(51) Int. Cl.
*A61B 5/024* (2006.01)
*A61B 5/352* (2021.01)
*A61B 5/353* (2021.01)
*A61N 1/365* (2006.01)

(52) U.S. Cl.
CPC .......... *A61B 5/024* (2013.01); *A61N 1/36578* (2013.01); *A61N 1/36592* (2013.01); *A61B 5/352* (2021.01); *A61B 5/353* (2021.01)

(58) Field of Classification Search
CPC ......... A61B 5/024; A61B 5/353; A61B 5/352; A61N 1/36578; A61N 1/36592
See application file for complete search history.

(56) References Cited

U.S. PATENT DOCUMENTS

| | | | |
|---|---|---|---|
| 4,485,813 | A | 12/1984 | Anderson et al. |
| 5,052,388 | A | 10/1991 | Sivula et al. |
| 5,292,341 | A | 3/1994 | Snell |
| 5,480,412 | A | 1/1996 | Mouchawar et al. |
| 5,507,782 | A | 4/1996 | Kieval et al. |
| 5,593,431 | A | 1/1997 | Sheldon |
| 5,683,432 | A | 11/1997 | Goedeke et al. |
| 5,720,769 | A | 2/1998 | van Oort et al. |

(Continued)

FOREIGN PATENT DOCUMENTS

| | | | |
|---|---|---|---|
| WO | 2016014352 | A1 | 1/2016 |
| WO | 2018165289 | A1 | 9/2018 |
| WO | 2020006361 | A1 | 1/2020 |

OTHER PUBLICATIONS

A0001332WO01 (PCT/IB2023/051289) PCT Notification of Transmittal of the International Search Report and the Written Opinion of the International Searching Authority, Mailed May 11, 2023, 12 pages.

*Primary Examiner* — Lindsey G Wehrheim

(57) ABSTRACT

A medical device having a motion sensor is configured to sense a motion signal, generate ventricular pacing pulses in a non-atrial tracking ventricular pacing mode and detect atrial event signals from the motion signal during the non-atrial tracking ventricular pacing mode. The medical device may be configured to determine atrial event intervals from the detected atrial event signals, determine a frequency distribution of the determined atrial event intervals and determine an atrial rate based on the frequency distribution of the detected atrial event intervals.

23 Claims, 13 Drawing Sheets

(56) References Cited

U.S. PATENT DOCUMENTS

| | | | |
|---|---|---|---|
| 5,885,471 | A | 3/1999 | Ruben et al. |
| 6,044,297 | A | 3/2000 | Sheldon et al. |
| 6,295,471 | B1 | 9/2001 | Bornzin et al. |
| 6,625,490 | B1 | 9/2003 | McClure et al. |
| 7,062,328 | B1 | 6/2006 | Levine et al. |
| 7,130,681 | B2 | 10/2006 | Gebhardt et al. |
| 7,483,745 | B2 | 1/2009 | Amblard |
| 7,689,283 | B1 | 3/2010 | Schecter |
| 7,848,807 | B2 | 12/2010 | Wang |
| 7,869,876 | B2 | 1/2011 | Prakash et al. |
| 8,135,463 | B2 | 3/2012 | Burnes et al. |
| 8,214,036 | B2 | 7/2012 | Casset |
| 8,233,981 | B2 | 7/2012 | Casset |
| 8,380,308 | B2 | 2/2013 | Rosenberg et al. |
| 8,433,409 | B2 | 4/2013 | Johnson et al. |
| 8,478,388 | B2 | 7/2013 | Nguyen et al. |
| 8,532,785 | B1 | 9/2013 | Crutchfield et al. |
| 8,541,131 | B2 | 9/2013 | Lund et al. |
| 8,700,181 | B2 | 4/2014 | Bornzin et al. |
| 8,831,705 | B2 | 9/2014 | Dobak |
| 8,909,329 | B2 | 12/2014 | Prakash et al. |
| 8,923,963 | B2 | 12/2014 | Bonner et al. |
| 8,996,109 | B2 | 3/2015 | Karst et al. |
| 9,272,146 | B2 | 3/2016 | Anselmi |
| 9,278,218 | B2 | 3/2016 | Karst et al. |
| 9,399,140 | B2 | 7/2016 | Cho et al. |
| 9,724,518 | B2 | 8/2017 | Sheldon et al. |
| 9,775,982 | B2 | 10/2017 | Grubac et al. |
| 10,080,900 | B2 | 9/2018 | Ghosh et al. |
| 10,207,116 | B2 | 2/2019 | Sheldon et al. |
| 10,286,214 | B2 | 5/2019 | Demmer et al. |
| 10,328,270 | B2 | 6/2019 | Demmer et al. |
| 10,449,366 | B2 | 10/2019 | Splett et al. |
| 10,532,212 | B2 | 1/2020 | Splett et al. |
| 10,617,873 | B2 | 4/2020 | Stahmann et al. |
| 11,478,653 | B2 | 10/2022 | Yang et al. |
| 2006/0161211 | A1 | 7/2006 | Thompson et al. |
| 2008/0021336 | A1 | 1/2008 | Dobak, III |
| 2009/0198299 | A1 | 8/2009 | Yu et al. |
| 2012/0095521 | A1 | 4/2012 | Hintz |
| 2014/0121720 | A1 | 5/2014 | Bonner et al. |
| 2015/0173655 | A1 | 6/2015 | Demmer et al. |
| 2016/0015984 | A1 | 1/2016 | Demmer et al. |
| 2016/0023000 | A1 | 1/2016 | Cho et al. |
| 2016/0067486 | A1 | 3/2016 | Brown et al. |
| 2016/0067487 | A1 | 3/2016 | Demmer et al. |
| 2016/0114161 | A1 | 4/2016 | Amblard et al. |
| 2017/0274213 | A1 | 9/2017 | Ghosh et al. |
| 2018/0085588 | A1 | 3/2018 | Splett et al. |
| 2018/0085589 | A1 | 3/2018 | Splett et al. |
| 2018/0117337 | A1 | 5/2018 | Demmer et al. |
| 2018/0154154 | A1 | 6/2018 | Sheldon et al. |
| 2018/0161580 | A1 | 6/2018 | Demmer et al. |
| 2019/0167972 | A1 | 6/2019 | Stahmann et al. |
| 2020/0146580 | A1* | 5/2020 | Sarkar .................. A61N 1/3956 |
| 2020/0179707 | A1 | 6/2020 | Splett et al. |
| 2020/0179708 | A1 | 6/2020 | Splett et al. |
| 2020/0376282 | A1* | 12/2020 | Bornzin ................. A61B 5/353 |
| 2021/0236825 | A1 | 8/2021 | Sheldon et al. |
| 2021/0236826 | A1 | 8/2021 | Sheldon et al. |
| 2022/0323768 | A1 | 10/2022 | Sheldon et al. |

* cited by examiner

600

650

METHOD AND APPARATUS FOR DETERMINING HEART RATE

REFERENCE TO RELATED APPLICATION

This application claims the benefit of provisional U.S. Patent Application No. 63/312,367, filed on Feb. 21, 2022, incorporated herein by reference in its entirety.

TECHNICAL FIELD

This disclosure relates to a medical device and method for determining a heart rate from a motion sensor signal.

BACKGROUND

During normal sinus rhythm (NSR), the heartbeat is regulated by electrical signals produced by the sino-atrial (SA) node located in the right atrial wall. Each intrinsic atrial depolarization signal produced by the SA node spreads across the atria, causing the depolarization and contraction of the atria, and arrives at the atrioventricular (AV) node. The AV node responds by propagating a ventricular depolarization signal through the Bundle of His (or "His bundle") of the ventricular septum and thereafter to the Purkinje branches and the Purkinje muscle fibers of the right and left ventricles. This native conduction system including the His bundle, right and left branches (sometimes referred to as the right and left bundle branches) and the Purkinje fibers may be referred to as the "His-Purkinje conduction system" or "His-Purkinje system." The heart rate arising from the SA node can be referred to as the "sinus rate."

Patients with a conduction system abnormality, e.g., poor AV node conduction, poor SA node function, or other conduction abnormalities, may receive a pacemaker to restore a more normal heart rhythm and AV synchrony. Ventricular pacing may be performed to maintain the ventricular rate in a patient having atrioventricular conduction abnormalities. A single chamber ventricular pacemaker may be coupled to a transvenous ventricular lead carrying electrodes placed in the right ventricle, e.g., in the right ventricular apex. The pacemaker itself can be implanted in a subcutaneous pocket with the transvenous ventricular lead tunneled to the subcutaneous pocket. Leadless, intracardiac pacemakers have been proposed or are commercially available for implantation entirely within a heart chamber, eliminating the need for transvenous leads. An intracardiac pacemaker may provide sensing and pacing from within a chamber of the patient's heart.

For example, a leadless intracardiac pacemaker may be implanted in a heart chamber of a patient having AV conduction block to deliver ventricular pacing to provide ventricular rate support. Such a pacemaker may sense R-wave signals attendant to intrinsic ventricular depolarizations and deliver ventricular pacing pulses in the absence of sensed R-waves. While single chamber ventricular sensing and pacing by an intracardiac ventricular pacemaker may adequately address some patient conditions, some patients may benefit from atrial and ventricular (dual chamber) sensing for providing atrial-synchronized ventricular pacing in order to maintain a regular heart rhythm.

SUMMARY

The techniques of this disclosure generally relate to a pacemaker configured to determine an atrial rate from a cardiac signal. The cardiac signal may be a cardiac mechanical signal representative of cardiac motion due to heart chamber contraction and relaxation and associated heart valve opening and closure. The cardiac signal is sensed by a sensor of the pacemaker. In some examples, a cardiac motion signal is sensed as an acceleration signal by an accelerometer of the pacemaker. The pacemaker may be configured to sense cardiac event signals from the motion signal and determine an atrial rate based the sensed cardiac event signals. The pacemaker may be a ventricular pacemaker configured to be implanted in or on a heart chamber for delivering atrial synchronous ventricular pacing by sensing atrial event signals and delivering ventricular pacing pulses in response to sensing the atrial event signals.

A ventricular pacemaker operating according to the techniques disclosed herein delivers ventricular pacing pulses in a non-atrial tracking (asynchronous) ventricular pacing mode, senses event signals from a cardiac motion signal during the non-atrial tracking pacing mode and determines an atrial rate from the sensed event signals. The atrial rate may be determined by determining sensed event intervals between consecutively sensed event signals, determining a frequency distribution of the sensed event intervals and identifying harmonics of the sensed event intervals. The atrial rate may be estimated by the pacemaker based on the identified harmonics of the sensed event intervals. In some examples, the pacemaker is configured to adjust an atrial event sensing control parameter or other pacemaker control parameter based on the determined atrial rate.

In one example, the disclosure provides a pacemaker including a motion sensor configured to sense a motion signal, a pulse generator configured to generate ventricular pacing pulses and a control circuit in communication with the motion sensor and the pulse generator. The control circuit is configured to control the pulse generator to generate pacing pulses in a non-atrial tracking ventricular pacing mode, sense atrial event signals from the motion signal sensed by the motion sensor during the non-atrial tracking ventricular pacing mode. The control circuit may determine atrial event intervals from the sensed atrial event signals, determine a frequency distribution of the determined atrial event intervals, and determine an atrial rate interval based on the frequency distribution of the atrial event intervals. The control circuit may set at least one control parameter based on the determined atrial rate interval. The at least one control parameter can be used by the control circuit during an atrial synchronous ventricular pacing mode. The control circuit may control the pulse generator to generate ventricular pacing pulses according to the atrial synchronous ventricular pacing mode in accordance with the at least one control parameter set based on the determined atrial rate interval.

In another example, the disclosure provides a method including sensing a motion signal, generating pacing pulses in a non-atrial tracking ventricular pacing mode, and sensing atrial event signals from the motion signal during the non-atrial tracking ventricular pacing mode. The method includes determining atrial event intervals from the sensed atrial event signals, determining a frequency distribution of the determined atrial event intervals, and determining an atrial rate interval based on the frequency distribution of the atrial event intervals. The method may include setting at least one control parameter based on the determined atrial rate interval and using the at least one control parameter used during an atrial synchronous ventricular pacing mode. The method can include generating ventricular pacing pulses according to the atrial synchronous ventricular pacing mode using the at least one control parameter set based on the determined atrial rate interval.

In another example, the disclosure provides a non-transitory, computer-readable storage medium comprising a set of instructions which, when executed by a control circuit of a pacemaker, cause the pacemaker to sense a motion signal, generate pacing pulses in a non-atrial tracking ventricular pacing mode, detect atrial event signals from the motion signal during the non-atrial tracking ventricular pacing mode, and determine atrial event intervals from the detected atrial event signals. The instructions may further cause the pacemaker to determine a frequency distribution of the determined atrial event intervals and determine an atrial rate interval based on the frequency distribution of the detected atrial event intervals. The instructions may further cause the pacemaker to set at least one control parameter based on the determined atrial rate interval that can be used by the control circuit during an atrial synchronous ventricular pacing mode. The instructions may cause the pacemaker to generate ventricular pacing pulses according to the atrial synchronous ventricular pacing mode using the at least one control parameter based on the determined atrial rate interval.

Further disclosed herein is the subject matter of the following clauses:

Clause 1. A medical device comprising a motion sensor configured to sense a motion signal, a pulse generator configured to generate ventricular pacing pulses, and a control circuit configured to control the pulse generator to generate pacing pulses in a non-atrial tracking ventricular pacing mode. The control circuit is further configured to sense atrial event signals from the motion signal sensed by the motion sensor during the non-atrial tracking ventricular pacing mode, determine atrial event intervals from the sensed atrial event signals, determine a frequency distribution of the determined atrial event intervals, determine an atrial rate interval based on the frequency distribution of the atrial event intervals, set at least one control parameter based on the determined atrial rate interval, the at least one control parameter being used by the control circuit during an atrial synchronous ventricular pacing mode, and control the pulse generator to generate ventricular pacing pulses according to the atrial synchronous ventricular pacing mode.

Clause 2. The medical device of clause 1 wherein the control circuit is further configured to determine the atrial rate interval based on the frequency distribution of the atrial event intervals by determining a harmonic relationship between the atrial event intervals based on the frequency distribution and determining the atrial rate interval based on the harmonic relationship of the determined atrial event intervals.

Clause 3. The medical device of clause 2 wherein the control circuit is further configured to determine the harmonic relationship by determining a first harmonic relationship of the atrial event intervals and a second harmonic relationship of the atrial event intervals, select a best fit harmonic relationship to the atrial event intervals from among the first harmonic relationship and the second harmonic relationship, determine a fundamental period of the selected best fit harmonic relationship, and determine the atrial rate interval based on the fundamental period.

Clause 4. The medical device of clause 3 wherein the control circuit is further configured to select the best fit harmonic relationship by at least one of: a) determining a goodness of fit measurement of each of the first harmonic relationship and the second harmonic relationship and selecting the best fit harmonic relationship based on the goodness of fit measurement, and b) determining a systolic event time interval from the motion signal and selecting the best fit harmonic relationship based on the systolic event time interval.

Clause 5. The medical device of any of clauses 3-4 wherein the control circuit is further configured to identify a first peak of the frequency distribution of the atrial event intervals, determine a representative atrial event interval associated with the first peak of the frequency distribution, determine the first harmonic relationship of the atrial event intervals by setting the representative atrial event interval equal to a first harmonic, and determine the second harmonic relationship of the atrial event intervals by setting the representative atrial event interval associated with the first peak of the frequency distribution equal to a second harmonic.

Clause 6. The medical device of any of clauses 1-5 wherein the control circuit is further configured to set a total time window for sensing the atrial event signal from the motion signal during each of a plurality of cardiac cycles, determine that less than a threshold number of atrial event intervals are determined from the sensed atrial event signals, and increase a duration of the total time window in response to determining that less than the threshold number of atrial event intervals are determined from the sensed atrial event signals.

Clause 7. The medical device of any of clauses 1-6 wherein the control circuit is further configured to set a ventricular event window ending time, set an atrial event sensing threshold amplitude by setting a first threshold amplitude applied to the motion signal before the ventricular event window ending time and setting a second threshold amplitude lower than the first threshold amplitude, the second threshold amplitude applied to the motion signal after the ventricular event window ending time, and sense atrial event signals from the motion signal sensed by the motion sensor during the non-atrial tracking ventricular pacing mode in response to the motion signal crossing one of the first threshold amplitude or the second threshold amplitude.

Clause 8. The medical device of any of clauses 1-7 wherein the control circuit is further configured to set the at least one control parameter by setting an atrial event sensing control parameter and detect an atrial event signal from the motion signal based on the atrial event sensing control parameter during the atrial synchronous ventricular pacing mode. The control circuit may be further configured to set an atrioventricular pacing interval in response to detecting the atrial event signal from the motion signal during the atrial synchronous ventricular pacing mode and determine that the atrioventricular pacing interval expires. The pulse generator is configured to generate a ventricular pacing pulse in response to the atrioventricular pacing interval expiring.

Clause 9. The medical device of clause 8 wherein the control circuit is further configured to set a ventricular event window having an ending time, set the at least one control parameter by setting a maximum ending time of the ventricular event window, adjust the ending time of the ventricular event window up to the maximum ending time, set an atrial event sensing threshold amplitude, and detect the atrial event signal in response to the motion signal crossing the atrial event sensing threshold amplitude during the ventricular event window.

Clause 10. The medical device of any of clauses 1-9 wherein the control circuit is further configured to set the at least one control parameter based on the determined atrial rate interval by setting a rate smoothing increment based on the atrial rate interval, set a rate smoothing interval using the rate smoothing increment, identify a ventricular event during the atrial synchronous ventricular pacing mode, and start a ventricular pacing escape interval set to the rate smoothing interval in response to identifying the ventricular event.

Clause 11. The medical device of any of clauses 1-10 wherein the control circuit is further configured to set the at least one control parameter based on the determined atrial rate interval by determining a ventricular rate interval during the atrial synchronous ventricular pacing mode, determining that the ventricular rate interval is different than the atrial rate interval, and setting the at least one control parameter by adjusting an atrial event sensing control parameter in response to the ventricular rate interval being different than the atrial rate interval.

Clause 12. The medical device of clause 11 wherein the control circuit is further configured to set the atrial event sensing control parameter by adjusting an atrial event sensing threshold amplitude.

Clause 13. The medical device of any of clauses 11-12 further comprising a cardiac electrical signal sensing circuit configured to sense atrial P-waves, and the control circuit is further configured to adjust the atrial event sensing control parameter by adjusting a P-wave sensing control parameter in response to the ventricular rate interval being different than the atrial rate interval.

Clause 14. The medical device of clause 11 wherein the control circuit is further configured to set a ventricular event window ending time, set an atrial event sensing threshold amplitude by setting a first threshold amplitude applied to the motion signal before the ventricular event window ending time and setting a second threshold amplitude lower than the first threshold amplitude and applied to the motion signal after the ventricular event window ending time, and set the atrial event sensing control parameter in response to the ventricular rate interval being different than the atrial rate interval by adjusting at least one of the ventricular event window ending time, the first threshold amplitude and the second threshold amplitude.

Clause 15. The medical device of any of clauses 1-14 further comprising a housing enclosing the motion sensor, the pulse generator and the control circuit and a pair of electrodes on the housing and coupled to the pulse generator for delivering the ventricular pacing pulses.

Clause 16. The medical device of clause 15 wherein at least one electrode of the pair of electrodes is a tissue piercing electrode configured for delivering the ventricular pacing pulses.

Clause 17. The medical device of any of clauses 15-16, wherein at least one electrode of the pair of electrodes is configured to be implanted for delivering the ventricular pacing pulses to at least a portion of the His-Purkinje conduction system.

Clause 18. The medical device of any of clauses 15-17, wherein the housing is configured to be implanted in an atrial chamber.

Clause 19. A method comprising, sensing a motion signal, generating pacing pulses in a non-atrial tracking ventricular pacing mode, sensing atrial event signals from the motion signal during the non-atrial tracking ventricular pacing mode, determining atrial event intervals from the sensed atrial event signals, determining a frequency distribution of the determined atrial event intervals, determining an atrial rate interval based on the frequency distribution of the atrial event intervals. The method may further include setting at least one control parameter based on the determined atrial rate interval, where the at least one control parameter is used during an atrial synchronous ventricular pacing mode, and generating ventricular pacing pulses according to the atrial synchronous ventricular pacing mode.

Clause 20. The method of clause 19 further comprising determining the atrial rate interval based on the frequency distribution of the atrial event intervals by determining a harmonic relationship between the atrial event intervals based on the frequency distribution and determining the atrial rate interval based on the harmonic relationship of the determined atrial event intervals.

Clause 21. The method of clause 20, further comprising determining the harmonic relationship by determining a first harmonic relationship of the atrial event intervals and a second harmonic relationship of the atrial event intervals, selecting a best fit harmonic relationship to the atrial event intervals from among the first harmonic relationship and the second harmonic relationship, determining a fundamental period of the selected best fit harmonic relationship and determining the atrial rate interval based on the fundamental period.

Clause 22. The method of clause 21 wherein selecting the best fit harmonic relationship comprises at least one of: a) determining a goodness of fit measurement of each of the first harmonic relationship and the second harmonic relationship and selecting the best fit harmonic relationship based on the goodness of fit measurement, and b) determining a systolic event time interval from the motion signal and selecting the best fit harmonic relationship based on the systolic event time interval.

Clause 23. The method of any of clauses 21-22 further comprising identifying a first peak of the frequency distribution of the atrial event intervals, determining a representative atrial event interval associated with the first peak of the frequency distribution, determining the first harmonic relationship of the atrial event intervals by setting the representative atrial event interval equal to a first harmonic, and determining the second harmonic relationship of the atrial event intervals by setting the representative atrial event interval associated with the first peak of the frequency distribution equal to a second harmonic.

Clause 24. The method of any of clauses 19-23 further comprising setting a total time window for sensing the atrial event signal from the motion signal during each of a plurality of cardiac cycles, determining that less than a threshold number of atrial event intervals are determined from the sensed atrial event signals, and increasing a duration of the total time window in response to determining that less than the threshold number of atrial event intervals are determined from the sensed atrial event signals.

Clause 25. The method of any of clauses 19-24 further comprising setting a ventricular event window ending time, setting an atrial event sensing threshold amplitude by setting a first threshold amplitude applied to the motion signal before the ventricular event window ending time and setting a second threshold amplitude lower than the first threshold amplitude, the second threshold amplitude applied to the motion signal after the ventricular event window ending time. The method may further include sensing atrial event signals from the motion signal sensed by the motion sensor during the non-atrial tracking ventricular pacing mode in response to the motion signal crossing one of the first threshold amplitude or the second threshold amplitude.

Clause 26. The method of any of clauses 19-25 further comprising setting the at least one control parameter by setting an atrial event sensing control parameter, detecting an atrial event signal from the motion signal based on the atrial event sensing control parameter during the atrial synchronous ventricular pacing mode, setting an atrioventricular pacing interval in response to detecting the atrial event signal from the motion signal during the atrial synchronous ventricular pacing mode, determining that the atrioventricular pacing interval expires, and generating a ventricular pacing pulse in response to the atrioventricular pacing interval expiring.

Clause 27. The method of clause 26 further comprising setting a ventricular event window having an ending time, setting the at least one control parameter by setting a maximum ending time of the ventricular event window, adjusting the ending time of the ventricular event window up to the maximum ending time, setting a first atrial event sensing threshold amplitude, and detecting the atrial event signal in response to the motion signal crossing the first atrial event sensing threshold amplitude during the ventricular event window.

Clause 28. The method of any of clauses 19-27 further comprising setting the at least one control parameter by setting a rate smoothing increment based on the atrial rate interval, setting a rate smoothing interval using the rate smoothing increment, identifying a ventricular event during the atrial synchronous ventricular pacing mode, and starting a ventricular pacing escape interval set to the rate smoothing interval in response to identifying the ventricular event.

Clause 29. The method of any of clauses 19-27 further comprising setting the at least one control parameter based on the determined atrial rate interval by determining a ventricular rate during the atrial synchronous ventricular pacing mode, determining that the ventricular rate interval is different than the atrial rate interval, and setting the at least one control parameter by adjusting an atrial event sensing control parameter in response to the ventricular rate interval being different than the atrial rate interval.

Clause 30. The method of clause 29 further comprising adjusting the atrial event sensing control parameter by adjusting an atrial event sensing threshold amplitude.

Clause 31. The method of any of clauses 29-30 further comprising sensing a cardiac electrical signal, sensing atrial P-waves from the cardiac electrical signal, and adjusting the atrial event sensing control parameter by adjusting a P-wave sensing control parameter in response to the ventricular rate interval being different than the atrial rate interval.

Clause 32. The method of clause 29 further comprising setting a ventricular event window ending time, setting an atrial event sensing threshold amplitude by setting a first threshold amplitude applied to the motion signal before the ventricular event window ending time and setting a second threshold amplitude that is lower than the first threshold amplitude and applied to the motion signal after the ventricular event window ending time. The method may further include adjusting the atrial event sensing control parameter in response to the ventricular rate being different than the atrial rate by adjusting at least one of the ventricular event window ending time, the first threshold amplitude and the second threshold amplitude.

Clause 33. The method of any of clauses 19-32 further comprising delivering the ventricular pacing pulses via a pair of electrodes on a housing that encloses a motion sensor that is configured to sense the motion signal.

Clause 34. The method of clause 33 further comprising delivering the ventricular pacing pulses via a tissue piercing electrode.

Clause 35. The method of any of clauses 33-34 further comprising delivering the ventricular pacing pulses via an electrode that is configured to be implanted for pacing at least a portion of a His-Purkinje conduction system.

Clause 36. The method of any of clauses 33-35 further comprising delivering the ventricular pacing pulses when the housing is implanted in an atrial chamber.

Clause 37. A non-transitory, computer-readable storage medium comprising a set of instructions which, when executed by a control circuit of a medical device, cause the medical device to sense a motion signal, generate pacing pulses in a non-atrial tracking ventricular pacing mode, detect atrial event signals from the motion signal during the non-atrial tracking ventricular pacing mode, determine atrial event intervals from the detected atrial event signals, determine a frequency distribution of the determined atrial event intervals, determine an atrial rate interval based on the frequency distribution of the detected atrial event intervals. The instructions may further cause the medical device to set at least one control parameter based on the determined atrial rate interval, the at least one control parameter being used during an atrial synchronous ventricular pacing mode, and generate ventricular pacing pulses according to the atrial synchronous ventricular pacing mode.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
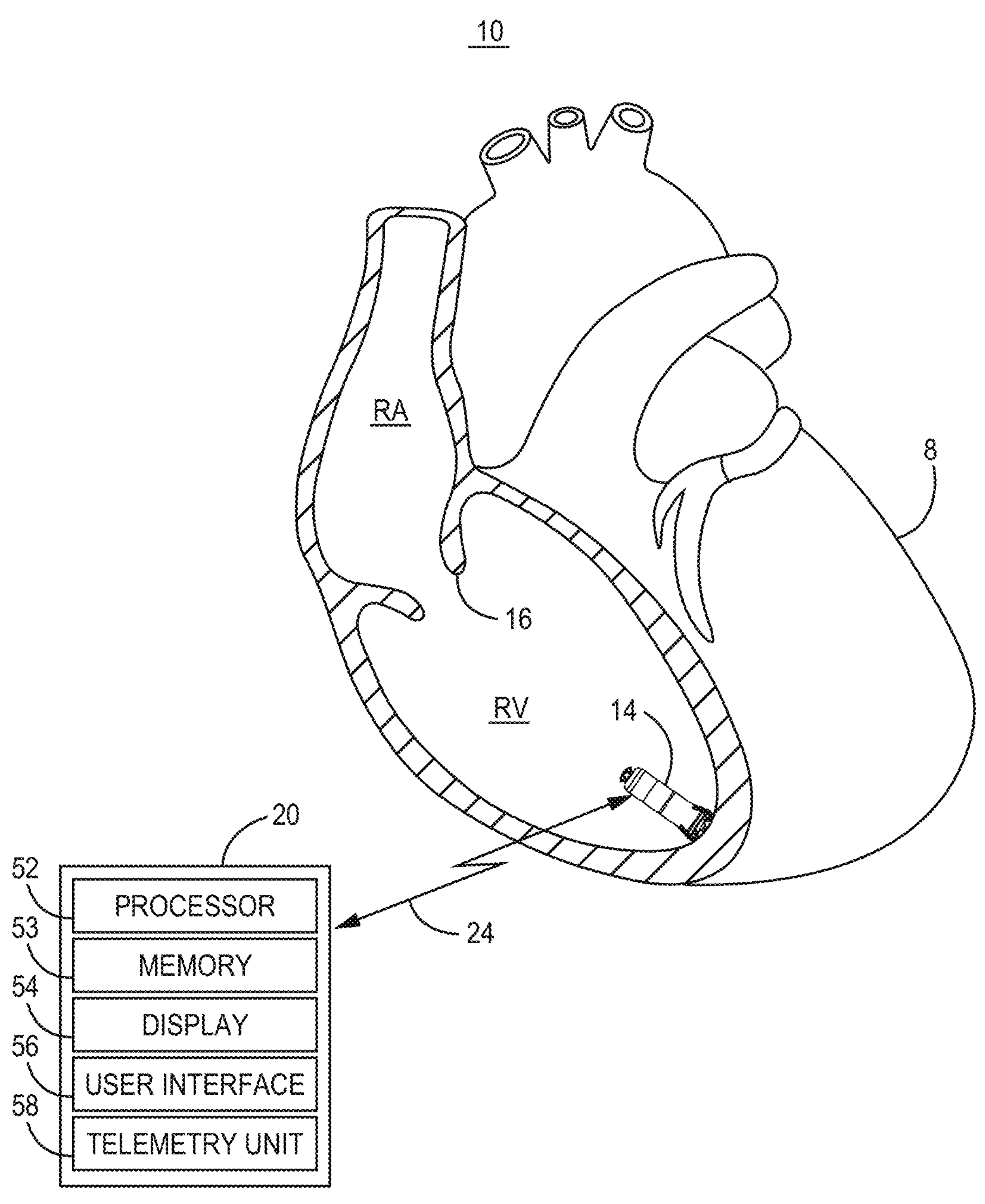
FIG. 1 is a conceptual diagram illustrating a medical device system that may be used to sense cardiac electrical signals and motion signals induced by cardiac motion and flowing blood and provide pacing therapy to a patient's heart.

In general, this disclosure describes techniques for determining an atrial rate from a motion signal sensed by a ventricular pacemaker. The atrial rate may be the sinus rate arising from the SA node. As described herein, atrial event signals may be sensed from a signal produced by a motion sensor that may be implanted in a ventricular location, e.g., in or on the right or left ventricle. The atrial event signals that may be detected from the motion sensor signal may correspond to motion caused by atrial mechanical contraction and the active filling phase of the ventricle, sometimes referred to as the "atrial kick." A ventricular pacemaker may be wholly implantable within a ventricular heart chamber, having a motion sensor for producing an intraventricular motion signal. Atrial event signals can be detected from within the ventricle for use in controlling atrial synchronized ventricular pacing, for example. In this way, atrial-synchronized ventricular pacing pulses can be delivered by a pacemaker implanted in the ventricle without requiring a sensor in or on the atria of the patient's heart for detecting atrial events.

The atrial event signals may be sensed by a ventricular pacemaker according to various sensing control parameters, which may include a selected motion sensor signal vector, sensing threshold amplitude(s), a post-ventricular atrial blanking period, a post-ventricular atrial refractory period, and time window(s) during which an atrial event can be sensed in response to a sensing threshold amplitude crossing. These various sensing control parameters may be programmable by a user and/or established by the pacemaker during a set up procedure, e.g., as generally disclosed in U.S. Patent Application Publication No. 2020/0179707 (Splett, et al.) and in U.S. Patent Application Publication No. 2020/0179708 (Splett, et al.), both of which are incorporated herein by reference in their entirety. After being initially programmed or set to starting values, the sensing control parameters may be adjusted by the pacemaker, e.g., based on analysis of the motion signal by processing and control circuitry of the pacemaker. Techniques for adjusting atrial event sensing control parameters are generally disclosed in U.S. Patent Application Publication No. 2021/0236825 (Sheldon, et al.) and in U.S. Patent Application Publication No. 2021/0236826 (Sheldon, et al.), both of which are incorporated herein by reference in their entirety.

Selecting, programming, and adjusting the atrial event sensing control parameters can be a challenging and time-consuming process. The selected setting of individual sensing control parameters alone and in combinations with other selected sensing control parameters can affect the reliability of sensing atrial event signals and the resulting effectiveness and benefit of atrial synchronous ventricular pacing. Changes in physiological conditions, such as heart rate, posture, physical activity, etc., can affect which settings are optimal for reliably sensing atrial event signals from the motion sensor signal. According to the techniques disclosed herein, the ventricular pacemaker may determine an atrial rate based on atrial event signals sensed from the motion signal. Determination of the atrial rate, which may be a sinus rate, can facilitate selection and adjustment of sensing control parameters for reliable atrial event signal sensing. Furthermore, knowing the atrial rate, the ventricular pacemaker may be able to determine if ventricular pacing pulses are appropriately tracking the atrial rate. Accordingly, the techniques disclosed herein provide improvements in a pacemaker configured to deliver ventricular pacing therapy, e.g., by improving atrial event sensing and monitoring of ventricular tracking of an atrial rate in a patient-specific manner that reduces the time and burden required by a clinician in monitoring the pacemaker performance and programming the pacing control parameters.

FIG. 1 is a conceptual diagram illustrating an implantable medical device (IMD) system 10 that may be used to sense cardiac electrical signals and motion signals induced by cardiac motion and flowing blood and provide pacing therapy to a patient's heart 8. IMD system 10 includes a pacemaker 14. Pacemaker 14 may be a transcatheter intracardiac pacemaker which is adapted for implantation wholly within a heart chamber, e.g., wholly within the right ventricle (RV) as shown or wholly within the left ventricle (LV) of heart 8 for sensing cardiac signals and delivering ventricular pacing pulses. Pacemaker 14 may be reduced in size compared to subcutaneously implanted pacemakers and may be generally cylindrical in shape to enable transvenous implantation via a delivery catheter.

Pacemaker 14 is shown positioned in the RV, along an endocardial wall, e.g., near the RV apex though other locations within the RV are possible. The techniques disclosed herein are not limited to the pacemaker location within the RV, however. Other positions within or on heart 8 are possible. Pacemaker 14 may be positioned in or on the RV or LV and configured to detect cardiac motion signals and deliver atrial-synchronized ventricular pacing to the RV or the LV using the techniques disclosed herein. Pacemaker 14 may be positioned within the RV or LV to provide respective right ventricular or left ventricular pacing and for sensing cardiac motion signals by a motion sensor within the ventricular chamber. In some examples, pacemaker 14 may be positioned along the interventricular septum for delivering ventricular pacing pulses to the left bundle branch and/or the right bundle branch of the ventricular conduction system also referred to as the "His-Purkinje system." In other examples, as described below in conjunction with FIG. 3, pacemaker 14 may be positioned in the right atrium (RA) for delivering pacing to the ventricular myocardium and/or the ventricular conduction system, e.g., to the His Bundle, from a right atrial approach.

Pacemaker 14 is capable of producing electrical stimulation pulses, e.g., pacing pulses, delivered to heart 8 via one or more electrodes on the outer housing of the pacemaker. Pacemaker 14 is configured to deliver RV pacing pulses and sense an RV cardiac electrical signal using leadless, housing based electrodes for producing an RV electrogram (EGM) signal. The cardiac electrical signals may be sensed using the housing based electrodes that are also used to deliver pacing pulses to the RV.

Pacemaker 14 is configured to control the delivery of ventricular pacing pulses to the RV in a manner that promotes synchrony between atrial activation and ventricular activation, e.g., by maintaining a target atrioventricular (AV) interval between atrial events and ventricular pacing pulses. That is, pacemaker 14 controls pacing pulse delivery to maintain a desired AV interval between atrial contractions corresponding to atrial systole and ventricular pacing pulses delivered to cause ventricular depolarization and ventricular systole.

According to the techniques described herein, atrial systolic events producing the active ventricular filling phase can be detected by pacemaker 14 from a motion sensor such as an accelerometer enclosed by the housing of pacemaker 14. The motion signal produced by an accelerometer implanted within a ventricular chamber, which may be referred to as an "intraventricular motion signal," may include motion signals caused by ventricular and atrial events. For example, acceleration of blood flowing into the RV through the tricuspid valve 16 between the RA and RV caused by atrial systole, and referred to as the "atrial kick," may be detected by pacemaker 14 from the signal produced by an accelerometer included in pacemaker 14. Other cardiac event signals that may be present in the motion sensor signal, such as motion caused by ventricular contraction and passive ventricular filling are described below in conjunction with FIG. 5.

Atrial P-waves that are attendant to atrial depolarizations are relatively low amplitude signals in the near-field ventricular cardiac electrical signal received by pacemaker 14 (e.g., compared to the near-field R-wave) and therefore can be difficult to reliably detect from the cardiac electrical signal acquired by pacemaker 14 when implanted in or on a ventricular chamber. Atrial-synchronized ventricular pacing by pacemaker 14 or other functions that rely on atrial sensing may not be reliable when based solely on a cardiac electrical signal received by pacemaker 14. According to the techniques disclosed herein, pacemaker 14 includes a motion sensor and is configured to detect an atrial event signal corresponding to atrial mechanical activation (e.g., atrial mechanical systole) from the signal produced by the motion sensor. Ventricular pacing pulses may be synchronized to the atrial event signal that is sensed from the motion sensor signal by setting a programmable AV pacing interval that controls the timing of the ventricular pacing pulse relative to the detected atrial systolic event.

A target AV interval may be a default value or a programmed value selected by a clinician and is the time interval from the detection of the atrial event until delivery of the ventricular pacing pulse. In some instances, the target AV interval may be started from the time the atrial systolic event is detected based on a motion sensor signal crossing a sensing threshold amplitude or starting from an identified fiducial point of the atrial event signal, e.g., a maximum peak amplitude. The target AV interval may be identified as being hemodynamically optimal for a given patient based on clinical testing or assessments of the patient or based on clinical data from a population of patients. The target AV interval may be determined to be optimal based on relative timing of electrical and mechanical events as identified from the cardiac electrical signal received by pacemaker 14 and the motion sensor signal received by pacemaker 14. The AV interval may be 10 to 50 ms and can be 10 to 20 ms in some examples.

Pacemaker 14 may be capable of bidirectional wireless communication with an external device 20 for programming the AV pacing interval and other pacing control parameters as well as cardiac event sensing control parameters, which may be utilized for sensing cardiac electrical events, e.g., R-waves attendant to ventricular depolarizations, and atrial event signals from the motion sensor signal. Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in pacemaker 14. External device 20 may be located in a clinic, hospital or other medical facility. External device 20 may alternatively be embodied as a home monitor or a handheld device that may be used in a medical facility, in the patient's home, or another location.

External device 20 may include a processor 52, memory 53, display 54, user interface 56 and telemetry unit 58. Processor 52 controls external device operations and processes data and signals received from pacemaker 14. Display unit 54 may generate a display, which may include a graphical user interface, of data and information relating to pacemaker functions to a user for reviewing pacemaker operation and programmed parameters as well as cardiac electrical signals, cardiac motion signals or other physiological data that may be acquired by pacemaker 14 and transmitted to external device 20 during an interrogation session.

User interface 56 may include a mouse, touch screen, keypad or the like to enable a user to interact with external device 20 to initiate a telemetry session with pacemaker 14 for retrieving data from and/or transmitting data to pacemaker 14, including programmable parameters for controlling cardiac event sensing and therapy delivery. Telemetry unit 58 includes a transceiver and antenna configured for bidirectional communication with a telemetry circuit included in pacemaker 14 and is configured to operate in conjunction with processor 52 for sending and receiving data relating to pacemaker functions via communication link 24.

At the time of implant, during patient follow-up visits, or any time after pacemaker implantation, pacemaker 14 may perform a set-up procedure to establish sensing control parameters used in detecting atrial events from the motion sensor signal. The patient may be standing, sitting, lying down or ambulatory during the process. The set-up procedure may include acquiring motion sensor signal data and generating distributions of motion sensor signal features for establishing atrial event sensing control parameters. Motion sensor signal data may be transmitted to external device 20 and displayed on display unit 54 of external device 20 in the form of a histogram in some examples. The atrial event sensing parameters established based on the motion sensor signal data may be set automatically or may be transmitted to external device 20 for generating a display on display unit

54 as recommended parameters, allowing a clinician to review and accept or modify the recommended parameters, e.g., using user interface 56.

In some examples, external device processor 52 may execute operations for establishing a starting value of an atrial event sensing control parameter based on data retrieved from pacemaker 14. Processor 52 may cause display unit 54 to generate a display of data relating to a motion sensor signal, including histogram distributions of metrics determined from a cardiac motion signal for use in selecting starting values of atrial event sensing control parameters. Display unit 54 may be a graphical user interface that enables a user to interact with the display, e.g., for selecting various displays or information for viewing. In some examples, a user may select one or more atrial event sensing control parameter settings to be automatically established by pacemaker 14 and/or may program starting sensing control parameters or other programmable parameters for controlling sensing operation and therapy delivery. Processing circuitry included in pacemaker 14 and/or processor 52 may determine starting values for one or more atrial event sensing control parameters based on data acquired from motion sensor signals produced by an accelerometer included in pacemaker 14 and various thresholds and criteria, which may include user programmable thresholds or criteria used in analyzing the motion sensor signal and setting the starting parameter values.

External device telemetry unit 58 is configured for bidirectional communication with implantable telemetry circuitry included in pacemaker 14. Telemetry unit 58 establishes a wireless communication link 24 with pacemaker 14. Communication link 24 may be established using a radio frequency (RF) link such as BLUETOOTH®, Wi-Fi, Medical Implant Communication Service (MICS) or other communication bandwidth. In some examples, external device 20 may include a programming head that is placed proximate pacemaker 14 to establish and maintain a communication link 24, and in other examples external device 20 and pacemaker 14 may be configured to communicate using a distance telemetry algorithm and circuitry that does not require the use of a programming head and does not require user intervention to maintain a communication link.

It is contemplated that external device 20 may be in wired or wireless connection to a communications network via a telemetry circuit that includes a transceiver and antenna or via a hardwired communication line for transferring data to a centralized database or computer to allow remote management of the patient. Remote patient management systems including a centralized patient database may be configured to utilize the presently disclosed techniques to enable a clinician to review EGM, motion sensor signal, and marker channel data and authorize programming of sensing and therapy control parameters in pacemaker 14, e.g., after viewing a visual representation of EGM, motion sensor signal and marker channel data.

Figure 2:
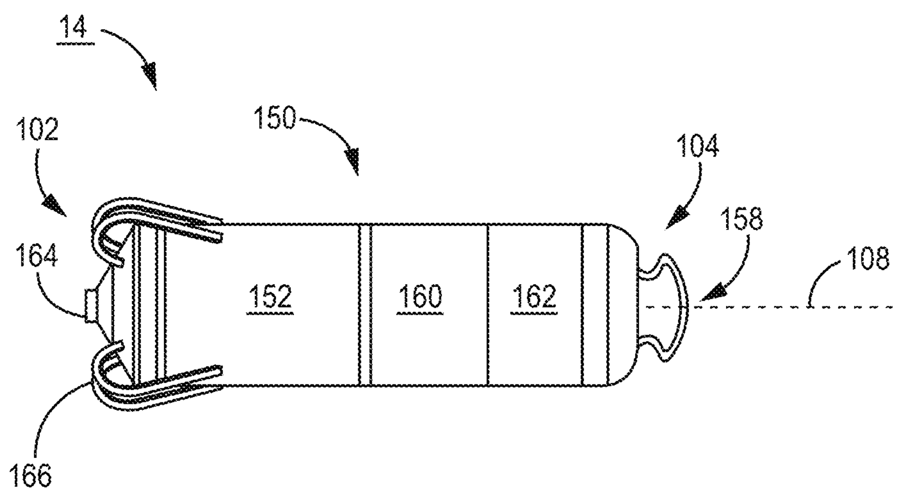
FIG. 2 is a conceptual diagram of the pacemaker shown in FIG. 1.

FIG. 2 is a conceptual diagram of the pacemaker 14 shown in FIG. 1 according to one example. Pacemaker 14 includes electrodes 162 and 164 spaced apart along the housing 150 of pacemaker 14 for sensing cardiac electrical signals and delivering pacing pulses. Electrode 164 is shown as a tip electrode extending from a distal end 102 of pacemaker 14, and electrode 162 is shown as a ring electrode along a mid-portion of housing 150, for example adjacent proximal end 104. Distal end 102 is referred to as "distal" in that it is expected to be the leading end as pacemaker 14 is advanced through a delivery tool, such as a catheter, and placed against a targeted pacing site.

Electrodes 162 and 164 form an anode and cathode pair for bipolar cardiac pacing and sensing. In alternative embodiments, pacemaker 14 may include two or more ring electrodes, two tip electrodes, and/or other types of electrodes exposed along pacemaker housing 150 for delivering electrical stimulation to heart 8 and sensing cardiac electrical signals. Electrodes 162 and 164 may be, without limitation, titanium, platinum, iridium or alloys thereof and may include a low polarizing coating, such as titanium nitride, iridium oxide, ruthenium oxide, platinum black, among others. Electrodes 162 and 164 may be positioned at locations along pacemaker 14 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide, among others. The entirety of the housing 150 may be insulated, but only electrodes 162 and 164 uninsulated. Electrode 164 may serve as a cathode electrode and be coupled to internal circuitry, e.g., a pacing pulse generator and cardiac electrical signal sensing circuitry, enclosed by housing 150 via an electrical feedthrough crossing housing 150. Electrode 162 may be formed as a conductive portion of housing 150 defining a ring electrode that is electrically isolated from the other portions of the housing 150 as generally shown in FIG. 2. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing.

The housing 150 may include a control electronics subassembly 152, which houses the electronics for sensing cardiac signals, producing pacing pulses and controlling therapy delivery and other functions of pacemaker 14, e.g., as described below in conjunction with FIG. 4. Housing 150 may further include a battery subassembly 160, enclosing one or more chargeable or non-rechargeable batteries, which provide power to the control electronics subassembly 152, such as the various circuits and components shown in FIG. 4.

A motion sensor may be implemented as an accelerometer enclosed within housing 150 in some examples. The accelerometer provides a signal to a processor included in control electronics subassembly 152 for signal processing and analysis for sensing atrial events, e.g., for use in controlling the timing of ventricular pacing pulses. As disclosed herein, event signals are sensed from the accelerometer signal for determining an atrial rate, which may be during a non-atrial tracking ventricular pacing mode. The atrial rate may be used in setting or adjusting sensing control parameters used for sensing atrial event signals, setting limits or ranges of auto-adjusting atrial event signals, and/or determining if the ventricular paced rate during an atrial synchronous ventricular pacing mode is tracking the determined atrial rate.

The accelerometer may be a three-dimensional accelerometer. In some examples, the accelerometer may have one "longitudinal" axis that is parallel to or aligned with the longitudinal axis 108 of pacemaker 14 and two orthogonal axes that extend in radial directions relative to the longitudinal axis 108. Practice of the techniques disclosed herein, however, are not limited to a particular orientation of the accelerometer within or along housing 150. In other examples, a one-dimensional accelerometer may be used to obtain a cardiac motion signal from which atrial event signals can be sensed. In still other examples, a two dimensional accelerometer or another multi-dimensional accelerometer may be used. Each axis of a single or multi-dimensional accelerometer may be defined by a piezoelectric element, micro-electrical mechanical system (MEMS) device or other sensor element capable of producing an electrical signal in response to changes in acceleration imparted on the sensor element, e.g., by converting the acceleration to a force or displacement that is converted to the electrical signal. In a multi-dimensional accelerometer, the sensor elements may be arranged orthogonally with each sensor element axis orthogonal relative to the other sensor element axes. Orthogonal arrangement of the elements of a multi-axis accelerometer, however, is not necessarily required.

Each sensor element may produce an acceleration signal corresponding to a vector aligned with the axis of the sensor element. A vector signal of a multi-dimensional accelerometer (also referred to as a "multi-axis" accelerometer) may be selected for use in sensing atrial event signals. In various examples, one, two or all three axis signals produced by a three-dimensional accelerometer may be selected as a vector signal for use in detecting atrial event signals, e.g., for determining an atrial rate and in controlling atrial-synchronized ventricular pacing delivered by pacemaker 14.

Pacemaker 14 may include a set of fixation tines 166 to secure pacemaker 14 to patient tissue, e.g., by actively engaging with the ventricular endocardium and/or interacting with the ventricular trabeculae. Fixation tines 166 are configured to anchor pacemaker 14 to position electrode 164 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may optionally include a delivery tool interface 158. Delivery tool interface 158 may be located at the proximal end 104 of pacemaker 14 and is configured to connect to a delivery device, such as a catheter, used to position pacemaker 14 at an implant location during an implantation procedure, for example within a heart chamber.

Figure 3:
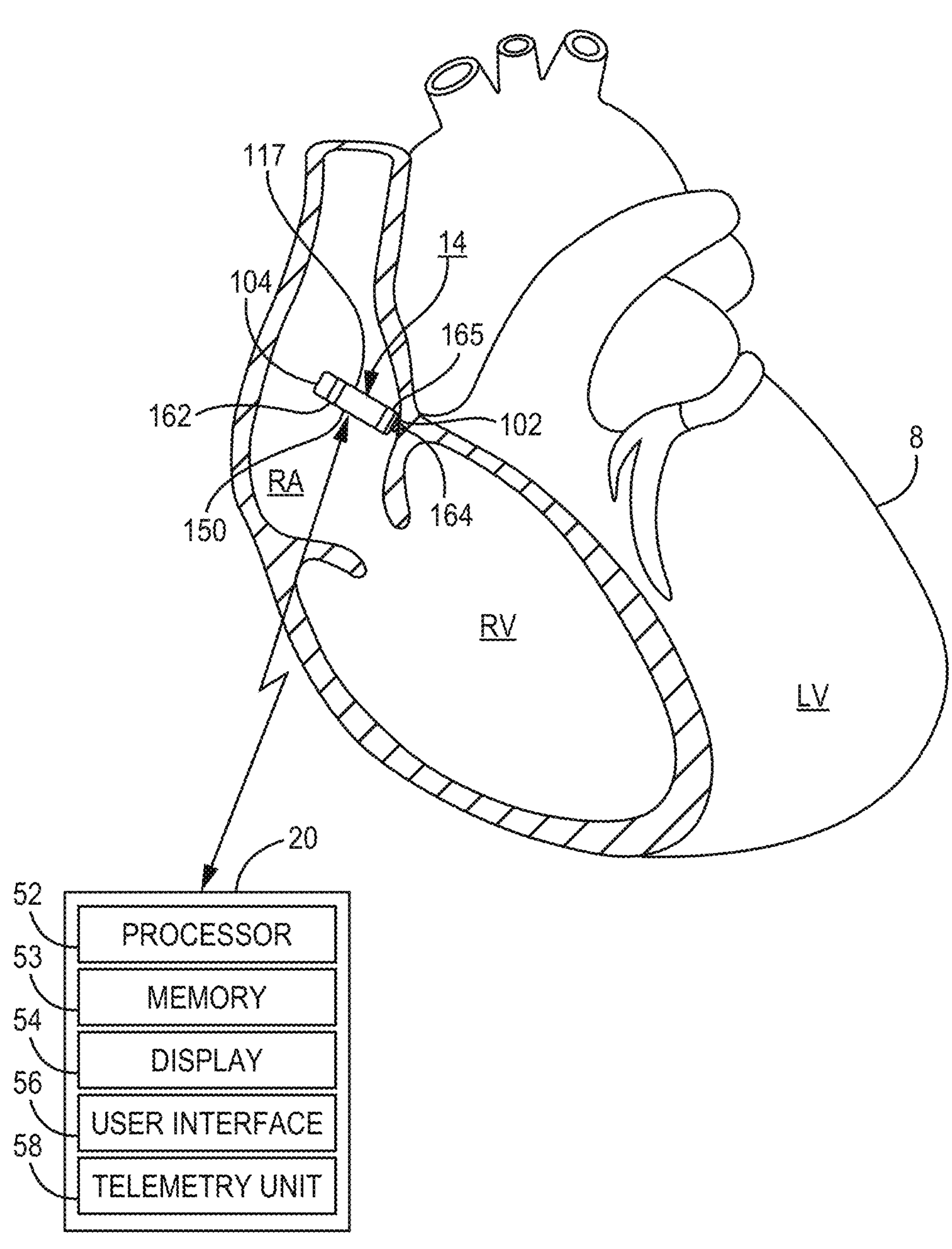
FIG. 3 is a conceptual diagram of a pacemaker implanted in an alternative location in a patient's heart for sensing cardiac signals and for delivering cardiac pacing pulses.

FIG. 3 is a conceptual diagram of pacemaker 14 implanted in an alternative location within the RA for sensing atrial electrical signals and for delivering cardiac pacing pulses. Pacemaker 14 may be positioned within the RA for providing ventricular pacing from an atrial implant location, which may include ventricular pacing of ventricular myocardium and/or via the native ventricular conduction system, which includes the His bundle, the right and left bundle branches and the Purkinje fibers and may be referred to as the "His-Purkinje system." Pacemaker 14 includes distal tip electrode 164, which in this example may be a tissue-piercing electrode, extending from the distal end 102 of the pacemaker housing 150. In FIG. 3, pacemaker 14 is shown implanted in the RA of the patient's heart to advance distal tip electrode 164 for delivering pacing pulses to ventricular tissue, which may be in or around the area of the His bundle of heart 8.

For example, the distal tip electrode 164 may be configured as a tissue piercing electrode that can be inserted into the inferior end of the interatrial septum, beneath the AV node and near the tricuspid valve annulus to position tip electrode 164 in ventricular tissue, which may be along or proximate to the His bundle. Distal tip electrode 164 may be a helical electrode, as shown in this example, providing fixation to anchor the pacemaker 14 at the implant position as well as deliver pacing pulses. In other examples, pacemaker 14 may include a fixation member that includes one or more tines (as shown in FIG. 1), hooks, barbs, helices or other fixation member(s) that anchor the distal end 102 of the pacemaker 14 at the implant site. Another example of a pacemaker that may be configured to operate according to the techniques disclosed herein for determining an atrial rate and is configured for delivering ventricular pacing from an atrial implant location is generally disclosed in U.S. Pat. No. 11,478,653 (Yang, et al.), incorporated herein by reference in its entirety.

A portion of the distal tip electrode 164 may be electrically insulated such that only the most distal end of tip electrode 164, furthest from housing distal end 102, is exposed to provide targeted pacing at a tissue site that may include ventricular myocardium and/or a portion of the His bundle. One or more housing-based electrodes 162 and 165 may be carried on the surface of the housing 150 of pacemaker 14. Electrodes 162 and 165 are shown as ring electrodes circumscribing the lateral sidewall 117 of pacemaker housing 150. Lateral sidewall 117 extends from distal end 102 to proximal end 104. In other examples, a return anode electrode used in sensing and pacing may be positioned on housing proximal end 104. Pacing of the ventricles may be achieved using the distal tip electrode 102 as the cathode electrode and either of the housing-based electrodes 162 or 165 as the return anode.

Cardiac electrical signals produced by heart 8 may be sensed by pacemaker 14 using a sensing electrode pair selected from electrodes 162, 164 and 165. For example, a cardiac electrical signal may be sensed using distal tip electrode 164 and distal housing-based electrode 165 or distal tip electrode 164 and proximal housing-based electrode 162. A second cardiac electrical signal may be sensed using electrodes 165 and 162. In other examples, a single cardiac electrical signal may be sensed using a single electrode pair selected from electrodes 162, 164 and 165.

Atrial synchronous or asynchronous ventricular pacing pulses may be delivered via electrodes 164 and 165, e.g., to capture at least a portion of ventricular myocardium and/or the His-Purkinje system. Pacemaker 14 may include an accelerometer that can be used to sense atrial event signals for delivering atrial synchronized ventricular pacing pulses. When implanted in the RA, however, atrial P-waves attendant to atrial depolarization may be sensed from a cardiac electrical signal sensed using housing-based electrodes, e.g., electrodes 165 and 162. Pacemaker 14 may be configured to deliver ventricular pacing pulses to the ventricular myocardial tissue and/or His bundle at an AV pacing interval following sensed P-waves in some examples.

The techniques disclosed herein for determining an atrial rate from a cardiac mechanical signal, e.g., an acceleration signal sensed by an accelerometer, however, may be used for determining an atrial rate during a non-atrial tracking ventricular pacing mode. The atrial rate may be used to confirm tracking of the ventricular pacing rate to the determined atrial rate during an atrial synchronous ventricular pacing mode, e.g., when far field oversensing of R-waves could be interfering with P-wave sensing by pacemaker 14. When the acceleration signal is used for sensing atrial event signals for controlling atrial synchronous ventricular pacing, determination of the atrial rate may be used for selecting or adjusting atrial event sensing parameters or other control parameters used by pacemaker 14 in delivering atrial synchronous ventricular pacing as described below in conjunction with the various diagrams and flow charts presented herein.

Figure 4:
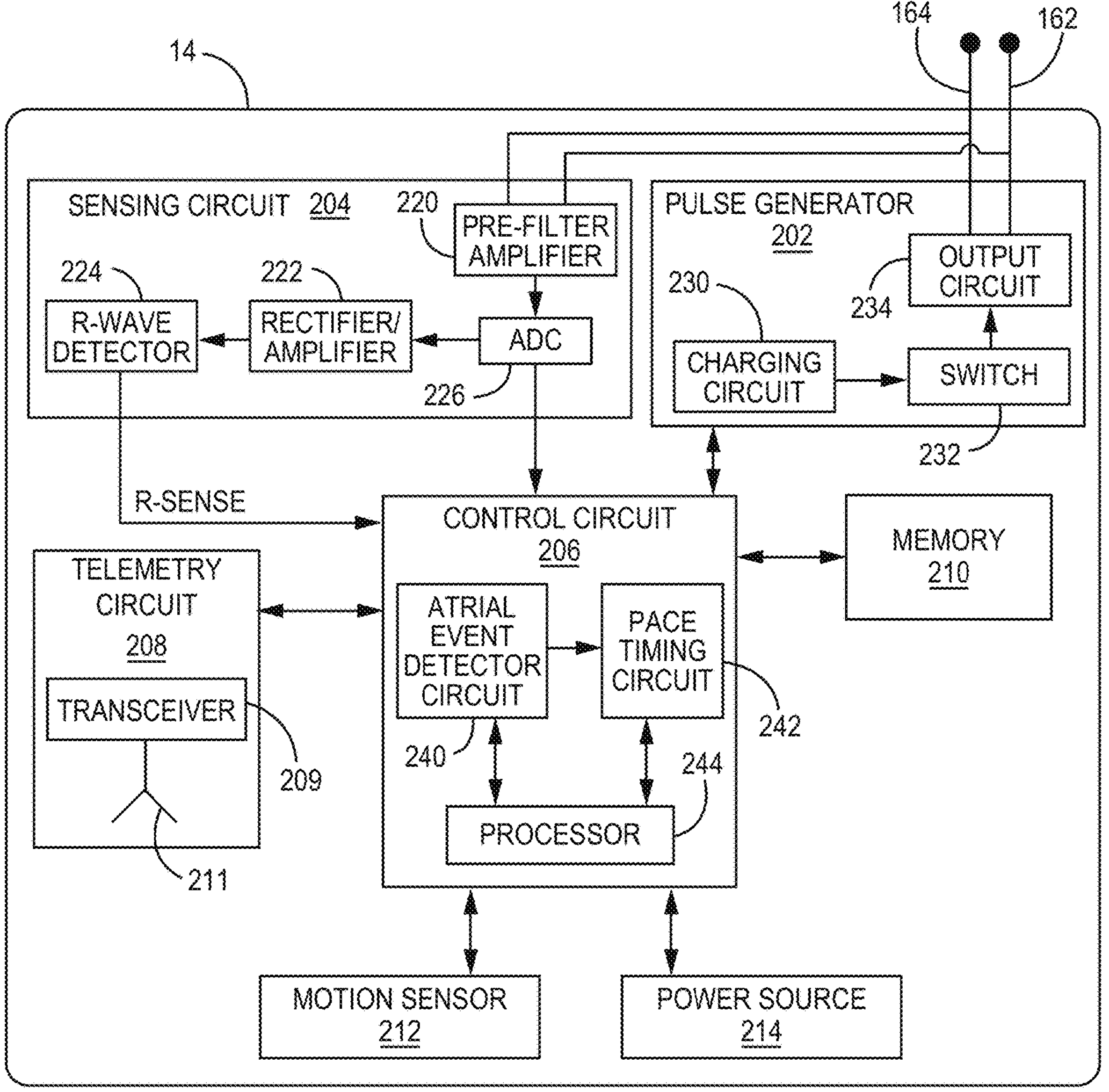
FIG. 4 is a schematic diagram of an example configuration of the pacemaker shown in FIG. 1.

FIG. 4 is a schematic diagram of an example configuration of pacemaker 14 shown in FIG. 1. Pacemaker 14 includes a pulse generator 202, a cardiac electrical signal sensing circuit 204 (also referred to herein as "sensing circuit" 204), a control circuit 206, memory 210, telemetry circuit 208, motion sensor 212 and a power source 214. The various circuits represented in FIG. 4 may be combined on one or more integrated circuit boards which include an application specific integrated circuit (ASIC), an electronic circuit, a processor (shared, dedicated, or group) and memory that execute one or more software or firmware programs, a combinational logic circuit, state machine or other suitable components that provide the described functionality.

Motion sensor 212 includes an accelerometer in the examples described herein. Examples of accelerometers that may be implemented in motion sensor 212 include piezoelectric sensors and MEMS devices. Motion sensor 212 is not limited to being an accelerometer, however. Other sensors may be utilized successfully in pacemaker 14 for sensing cardiac motion signals arising from the mechanical contraction and relaxation of the heart chambers for use in determining an atrial rate, such as blood flow sensors, impedance sensors (e.g., an impedance signal correlated to heart chamber volume changes), or pressure sensors according to the techniques described herein. As used herein, therefore, the term "motion sensor" refers to any sensor that produces a signal responsive to the mechanical motion of the heart chambers.

Motion sensor 212 may include a multi-axis sensor, e.g., a two-dimensional or three-dimensional sensor, with each axis providing an axis signal that may be analyzed individually or in combination for detecting cardiac mechanical events. Motion sensor 212 produces an electrical signal correlated to motion or vibration of sensor 212 (and pacemaker 14), e.g., when subjected to flowing blood and cardiac motion. The motion sensor 212 may include one or more filter, amplifier, rectifier, analog-to-digital converter (ADC) and/or other components for producing a motion signal that is passed to control circuit 206. For example, each vector signal produced by each selected individual axis of a multi-axis accelerometer may be filtered by a high pass filter, e.g., a 3 to 15 Hz high pass filter or a 10 Hz high pass filter. The filtered signal may be digitized by an ADC and rectified for use by atrial event detector circuit 240 for detecting atrial systolic events. The high pass filter may be lowered (e.g., to 5 Hz) if needed to detect atrial signals that have lower frequency content. In some examples, high pass filtering is performed with no low pass filtering. In other examples, each accelerometer axis signal is filtered by a low pass filter, e.g., a 25 Hz, 30 Hz or 40 Hz low pass filter, with or without high pass filtering.

One example of an accelerometer for use in implantable medical devices that may be implemented in conjunction with the techniques disclosed herein is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers that may be implemented in pacemaker 14 and used for detecting cardiac mechanical events using the presently disclosed techniques are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to acceleration forces imparted on pacemaker 14 due to ventricular and atrial events.

Sensing circuit 204 is configured to receive a cardiac electrical signal via electrodes 162 and 164 by a pre-filter and amplifier circuit 220. Pre-filter and amplifier circuit may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to analog-to-digital converter (ADC) 226. ADC 226 may pass a multi-bit, digital electrogram (EGM) signal to control circuit 206 for use by atrial event detector circuit 240 in identifying ventricular electrical events (e.g., R-waves or T-waves) and/or atrial electrical events, e.g., P-waves. Identification of cardiac electrical events, e.g., R-waves, may be used in algorithms for establishing atrial sensing control parameters and for detecting atrial systolic events from the motion sensor signal. The digital signal from ADC 226 may be passed to rectifier and amplifier circuit 222, which may include a rectifier, bandpass filter, and amplifier for passing a cardiac signal to R-wave detector 224.

R-wave detector 224 may include a sense amplifier or other detection circuitry that compares the incoming rectified, cardiac electrical signal to an R-wave sensing threshold, which may be an auto-adjusting threshold. When the incoming signal crosses the R-wave sensing threshold, the R-wave detector 224 produces an R-wave sensed event signal (R-sense) that is passed to control circuit 206. In other examples, R-wave detector 224 may receive the digital output of ADC 226 for detecting R-waves by a comparator, morphological signal analysis of the digital EGM signal or other R-wave detection techniques. Processor 244 may provide sensing control signals to sensing circuit 204, e.g., the R-wave sensing sensitivity and various blanking and refractory intervals applied to the cardiac electrical signal for controlling R-wave sensing. R-wave sensed event signals passed from R-wave detector 224 to control circuit 206 may be used for scheduling (or inhibiting) ventricular pacing pulses by pace timing circuit 242 and for use in identifying the timing of ventricular electrical events in algorithms performed by atrial event detector circuit 240 for detecting atrial event signals from an acceleration signal received from motion sensor 212.

For the sake of example, sensing circuit 204 is shown to include an R-wave detector 224 for sensing R-waves and generating R-wave sensed event signals. However, it is to be understood that in some examples, sensing circuit 204 may be configured to sense other cardiac electrical event signals, e.g., P-waves attendant to atrial depolarizations as described above in conjunction with FIG. 3 and below in conjunction with FIG. 12. For example, when pacemaker 14 is implanted in the RA as shown in FIG. 3, sensing circuit 204 may sense an atrial EGM signal from electrodes 165 and 162 and a ventricular EGM signal from electrodes 164 and 162. Sensing circuit 204 may include multiple sensing channels, e.g., an atrial sensing channel for sensing P-waves from the atrial EGM signal and a ventricular sensing channel for sensing R-waves from the ventricular EGM signal. P-waves may be sensed by P-wave detection circuitry in response to the sensed atrial EGM signal crossing a P-wave sensing threshold amplitude. The P-wave detection circuitry that may be included sensing circuit 204 may include a sense amplifier, comparator and/or other components or circuitry for detecting P-waves from a sensed electrical signal. A P-wave sensed event signal may be generated by sensing circuit 204 in response to a sensed P-wave and passed to control circuit 206 for use by pace timing circuit 242 in scheduling (or inhibiting) atrial pacing pulses when pacemaker 14 is configured for dual chamber pacing and sensing. The P-wave sensed event signal may be used by pace timing circuit 242 for triggering atrial synchronized ventricular pacing pulses at an AV pacing interval during atrial synchronous pacing modes.

Control circuit 206 includes an atrial event detector circuit 240, pace timing circuit 242, and processor 244. Control circuit 206 may receive R-wave sensed event signals and/or digital cardiac electrical signals from sensing circuit 204 for use in detecting and confirming cardiac events and controlling ventricular pacing. For example, R-wave sensed event signals may be passed to pace timing circuit 242 for inhibiting scheduled ventricular pacing pulses or scheduling ventricular pacing pulses when pacemaker 14 is operating in a non-atrial tracking ventricular pacing mode. R-wave sensed event signals may also be passed to atrial event detector circuit 240 for use in setting blanking periods, refractory periods, and atrial event sensing time windows used by control circuit 206 in detecting atrial event signals from the motion sensor signal.

Atrial event detector circuit 240 is configured to detect atrial event signals from a motion signal received from motion sensor 212. Atrial event detector circuit 240 may start a post-ventricular atrial blanking period and a post-ventricular atrial refractory period in response to a ventricular electrical event, e.g., an R-wave sensed event signal from sensing circuit 204 or delivery of a pacing pulse by pulse generator 202. The blanking period may correspond to a time period after the ventricular electrical event during which ventricular systolic events, e.g., corresponding to ventricular contraction are expected to occur. When ventricular pacing is properly synchronized to atrial events, an atrial event is not expected to occur during the blanking period, corresponding to ventricular systole. The atrial blanking period may be used to define a time period following a ventricular electrical event during which an atrial event signal is not sensed by atrial event detector circuit 240. The motion sensor signal may or may not be received or processed by control circuit 206 during the atrial blanking period. For example, during atrial event sensing for controlling atrial synchronous ventricular pacing, the motion sensor may be at least partially powered off to conserve power source 214 unless an active telemetry session is in progress such that the motion sensor signal may be received by control circuit 206, including during the blanking period, for transmission to external device 20 during a telemetry session.

Atrial event detector circuit 240 determines if the motion sensor signal satisfies atrial event detection criteria outside of the atrial blanking period. The motion sensor signal during the atrial blanking period may be monitored by atrial event detector circuit 240 for the purposes of detecting ventricular mechanical events, which may be used for confirming or validating atrial systolic event detection in some examples. As such, ventricular mechanical event detection windows may be set during the atrial blanking period and may be set according to predetermined time intervals following identification of a ventricular electrical event. Atrial event detector circuit 240 may be configured to detect one or more ventricular mechanical events, or at least detect motion signal peak amplitudes and/or threshold crossings, during the post-ventricular atrial blanking period and/or refractory period in some examples. The timing and detection of the ventricular mechanical events may be used to update the atrial blanking period or other atrial sensing control parameters and/or may be used to confirm detection of the atrial event occurring subsequent to expected ventricular mechanical events.

Atrial event detector circuit 240 may set a time window corresponding to the passive ventricular filling phase of a cardiac cycle based on the timing of a preceding ventricular electrical event, either an R-wave sensed event signal received from sensing circuit 204 or a ventricular pacing pulse delivered by pulse generator 202. A motion sensor signal crossing of an atrial event sensing threshold (also referred to herein as an "A4 sensing threshold") during or after the passive ventricular filling time window may be detected as the atrial event signal by atrial event detector circuit 240. As described below, two different atrial event sensing threshold values may be established for applying during the passive filling phase window (also referred to below as an "A3 window") and after the passive filling phase window (also referred to below as an "A4 window").

Atrial event detector circuit 240 passes an atrial event detection signal to processor 244 and/or pace timing circuit 242 in response to detecting an atrial event. Pace timing circuit 242 (or processor 244) may additionally receive R-wave sensed event signals from R-wave detector 224 for use in controlling the timing of pacing pulses delivered by pulse generator 202. Processor 244 may include one or more clocks for generating clock signals that are used by pace timing circuit 242 to time out an AV pacing interval that is started upon receipt of an atrial event detection signal from atrial event detector circuit 240 when control circuit 206 is operating in an atrial synchronous ventricular pacing mode, e.g., a VDD pacing mode. Pace timing circuit 242 may include one or more pacing escape interval timers or counters that are used to time out the AV pacing interval and other pacing escape intervals, e.g., a lower pacing rate interval. The AV pacing interval may be a programmable interval stored in memory 210 and retrieved by processor 244 for use in setting the AV pacing interval used by pace timing circuit 242. Pace timing circuit 242 may include a lower pacing rate interval timer for controlling a minimum ventricular pacing rate. For example, if an atrial systolic event is not detected from the motion sensor signal triggering a ventricular pacing pulse at the programmed AV pacing interval, a ventricular pacing pulse may be delivered by pulse generator 202 upon expiration of the lower pacing rate interval to prevent ventricular asystole and maintain a minimum ventricular rate.

One application of atrial sensed event signals produced by atrial event detector circuit 240 is for setting AV pacing intervals for controlling the timing of ventricular pacing pulses. Control circuit 206, however, may use atrial sensed event signals for other purposes. For example, pace timing circuit 242 may determine the time interval between consecutive atrial event signals sensed by atrial event detector circuit 240 for determining an atrial rate according to the techniques disclosed herein. At times, control circuit 206 may control pulse generator 202 in a non-atrial tracking ventricular pacing mode (also referred to as "asynchronous ventricular pacing"), which can be denoted as a VDI(R) or VVI(R) pacing mode. Ventricular pacing pulses are delivered in the absence of a sensed R-wave and inhibited in response to an R-wave sensed event signal from sensing circuit 204. During a process for determining an atrial rate for example, control circuit 206 may control pulse generator 202 to operate in a non-atrial tracking VDI pacing mode. Pace timing circuit 242 may time the intervals between consecutively sensed atrial event signals, referred to herein as "atrial event intervals," for use in determining the atrial rate using techniques disclosed herein.

Control circuit 206 may establish sensing control parameters used for detecting atrial event signals based on analysis of the motion signal sensed during a non-atrial tracking pacing mode. The non-atrial tracking ventricular pacing mode may be denoted as a VDI pacing mode in which ventricular pacing pulses are delivered or inhibited in response to sensing a ventricular event signal and dual chamber sensing of atrial and ventricular events is performed. Dual chamber sensing may be performed during the non-atrial tracking ventricular pacing mode by sensing ventricular electrical events by sensing circuit 204 and sensing atrial event signals from the motion signal received by atrial event detector circuit 240 from motion sensor 212. Atrial event sensing parameters established during a VDI pacing mode may include an atrial event sensing vector of the motion sensor producing a signal from which the atrial event is detected, the end of a passive ventricular filling window, and the A4 sensing threshold amplitude values applied during and after the passive ventricular filling window. In some examples, the atrial rate determined using the techniques disclosed herein can be used in establishing or adjusting the atrial event sensing control parameters.

Pulse generator 202 generates electrical pacing pulses that are delivered to the RV of the patient's heart via cathode electrode 164 and return anode electrode 162. In addition to providing control signals to pace timing circuit 242 and pulse generator 202 for controlling the timing of ventricular pacing pulses, processor 244 may retrieve programmable pacing control parameters, such as pacing pulse amplitude and pacing pulse width, which are passed to pulse generator 202 for controlling pacing pulse delivery. Pulse generator 202 may include charging circuit 230, switching circuit 232 and an output circuit 234.

Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of an AV pacing interval (or VV lower rate pacing interval) and kept closed for a programmed pacing pulse width to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration. Examples of pacing circuitry generally disclosed in U.S. Pat. No. 5,507,782 (Kieval, et al.) and in U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 206 and delivering a pacing pulse.

Memory 210 may include computer-readable instructions that, when executed by control circuit 206, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 may store timing intervals and other data used by control circuit 206 to control the delivery of pacing pulses by pulse generator 202, e.g., by detecting an atrial event by atrial event detector circuit 240 from the motion sensor signal and setting a pacing escape interval timer included in pace timing circuit 242, according to the techniques disclosed herein. Memory 210 may store atrial event intervals determined by control circuit 206 and used by control circuit 206 for determining an atrial rate.

Power source 214, which may be enclosed in battery subassembly 160 (FIG. 2), provides power to each of the other circuits and components of pacemaker 14 as required. Power source 214 may include one or more energy storage devices, such as one or more rechargeable or non-rechargeable batteries. The connections between power source 214 and other pacemaker circuits and components are not shown in FIG. 4 for the sake of clarity but are to be understood from the general block diagram of FIG. 4. For example, power source 214 may provide power as needed to charging and switching circuitry included in pulse generator 202, amplifiers, ADC 226 and other components of sensing circuit 204, telemetry circuit 208, memory 210, and motion sensor 212.

Telemetry circuit 208 includes a transceiver 209 and antenna 211 for wirelessly transmitting and receiving data, e.g., via a radio frequency (RF) communication link. Telemetry circuit 208 may be capable of bi-directional communication with external device 20 (FIG. 1) as described above. Motion sensor signals and cardiac electrical signals, and/or data derived therefrom may be transmitted by telemetry circuit 208 to external device 20. Programmable control parameters and algorithms for performing atrial event detection and ventricular pacing control may be received by telemetry circuit 208 and stored in memory 210 for access by control circuit 206.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, atrial event sensing from the motion sensor signal and ventricular pacing control operations performed by pacemaker 14 may be implemented in control circuit 206 executing instructions stored in memory 210 and relying on input from sensing circuit 204 and motion sensor 212. Providing software, hardware, and/or firmware to accomplish the described functionality in the context of any modern pacemaker, given the disclosure herein, is within the abilities of one of skill in the art.

Figure 5:
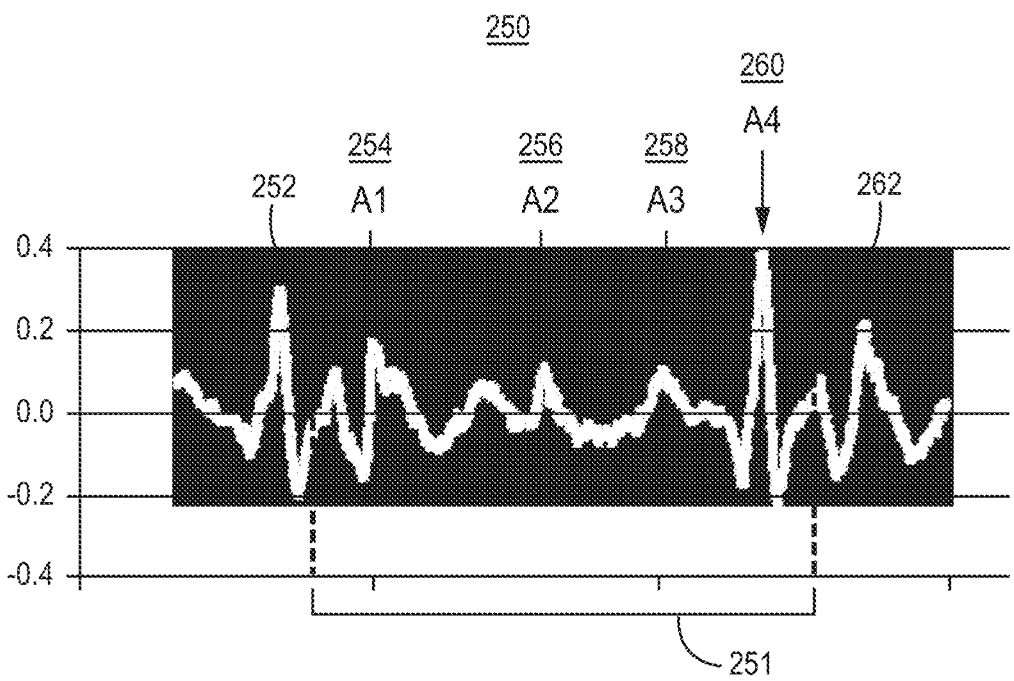
FIG. 5 is an example of a motion sensor signal that may be acquired by a motion sensor included in the pacemaker of FIG. 1 over a cardiac cycle.

FIG. 5 is an example of an acceleration signal 250 that may be acquired by motion sensor 212 over a cardiac cycle. Vertical dashed lines 252 and 262 denote the timing of two consecutive ventricular events (an intrinsic ventricular depolarization or a ventricular pacing pulse), marking the respective beginning and end of the ventricular cycle 251, including one ventricular systolic phase and one ventricular diastolic phase. The motion signal includes an A1 event 254, an A2 event 256, an A3 event 258 and an A4 event 260. The A1 event 254 is an acceleration signal (in this example when motion sensor 212 is implemented as an accelerometer) that occurs during ventricular contraction and marks the approximate onset of ventricular mechanical systole. The A1 event is also referred to herein as a "ventricular contraction event." The A2 event 256 is an acceleration signal that may occur with closure of the aortic and pulmonic valves, marking the approximate offset or end of ventricular mechanical systole. The A2 event may also mark the beginning of the isovolumic relaxation phase of the ventricles that occurs with aortic and pulmonic valve closure.

The A3 event 258 is an acceleration signal that occurs during passive ventricular filling and marks ventricular mechanical diastole. The A3 event is also referred to herein as the "A3 signal" and as the "ventricular passive filling event." Since the A2 event occurs with the end of ventricular systole, it is an indicator of the onset of ventricular diastole. The A3 event occurs during ventricular diastole. As such, the A2 and A3 events may be collectively referred to as ventricular mechanical diastolic events because they are both indicators of the ventricular diastolic period.

The A4 event 260 is an acceleration signal that occurs during atrial contraction and active ventricular filling and marks atrial mechanical systole. The A4 event 260 is also referred to herein as the "A4 signal" and is the "atrial event" or "atrial event signal" that is detected from motion sensor signal 250 by control circuit 206. For example, atrial event detector circuit 240 may detect A4 event 260. Processor 244 may control pace timing circuit 242 to trigger a ventricular pacing pulse by starting an AV pacing interval in response to atrial event detector circuit 240 detecting the A4 event 260 during an atrial synchronous ventricular pacing mode. During a non-atrial tracking ventricular pacing mode, control circuit 206 may determine features of the motion signal outside an atrial blanking period. Distributions of the features of the motion signal may be used in establishing atrial event sensing parameters, e.g., as generally described in the above-referenced U.S. Patent Application Publication No. 2020/0179707 (Splett, et al.) and in U.S. Patent Application Publication No. 2020/0179708 (Splett, et al.).

Figure 6:
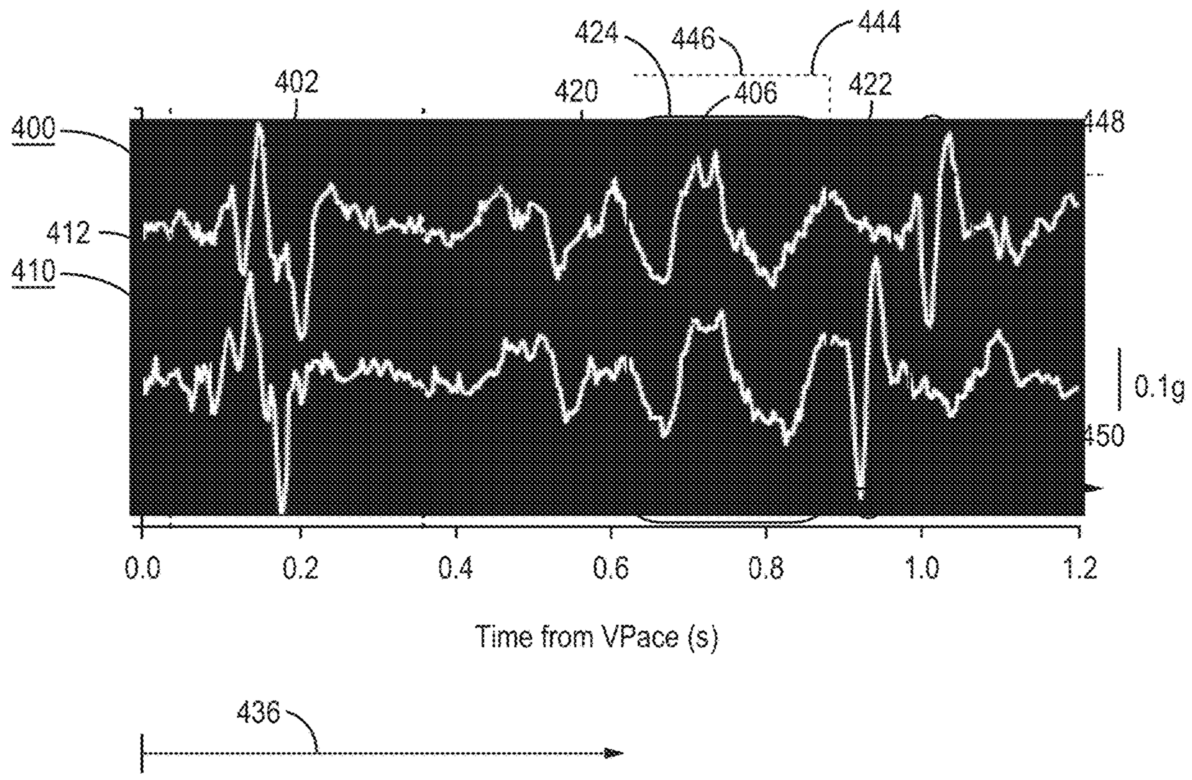
FIG. 6 is an example of motion sensor signals acquired over two different cardiac cycles.

FIG. 6 is an example of motion sensor signals 400 and 410 acquired over two different cardiac cycles. A ventricular pacing pulse is delivered at time 0.0 seconds for both cardiac cycles. The top sensor signal 400 is received over one cardiac cycle, and the bottom sensor signal 410 is received over a different cardiac cycle. Each cardiac cycle includes one phase of ventricular systole followed by one phase of ventricular diastole. The two signals 400 and 410 are aligned in time at 0.0 seconds, the time of the ventricular pacing pulse delivery. While motion signals 400 and 410 and motion signal 250 of FIG. 6 are shown as raw accelerometer signals, it is recognized that control circuit 206 may receive a digitized filtered, amplified and rectified signal from motion sensor 212 for processing and analysis as described in conjunction with the flow charts and histogram distributions presented in the accompanying drawings.

The A1 events 402 and 412 of the respective motion sensor signals 400 and 410, which occur during ventricular contraction, are observed to be well-aligned in time following the ventricular pacing pulse at time 0.0 seconds. Similarly, the A2 events 404 and 414 (which may mark the end of ventricular systole and the isovolumic ventricular relaxation phase) and the A3 events 406 and 416 (occurring during passive ventricular filling) are well-aligned in time. Since the A1, A2 and A3 events are ventricular events, occurring during ventricular contraction, at the end of ventricular systole and start of isovolumic ventricular relaxation and during passive ventricular filling, respectively, these events are expected to occur at relatively consistent intervals following a ventricular electrical event, the ventricular pacing pulse in this example, and relative to each other. The time relationship of the A1, A2 and A3 events may be different following a ventricular pacing pulse compared to following a sensed intrinsic R-wave. During a stable paced or intrinsic ventricular rhythm, however, the relative timing of ventricular A1, A2 and A3 events to each other and the immediately preceding ventricular electrical event is expected to be consistent from beat-to-beat.

The A4 events 408 and 418 of the first and second motion sensor signals 400 and 410, respectively, are not aligned in time. The A4 event occurs during atrial systole and as such the time interval of the A4 event following the immediately preceding ventricular electrical event (sensed R-wave or ventricular pacing pulse) and the preceding A1 through A3 events may vary between cardiac cycles. The timing of A4 events relative to ventricular events may vary as the atrial rate changes. The timing of A4 events relative to ventricular events may be highly variable during non-atrial tracking ventricular pacing modes.

The consistency of the timing of the A1 through A3 events relative to each other and the immediately preceding ventricular electrical event may be used for determining a post-ventricular atrial blanking period 436 and increasing confidence in reliably detecting A4 events 408 and 418. Control circuit 206 does not detect atrial event signals during the atrial blanking period 436, which may extend from the ventricular electrical event (at time 0.0) through an estimated onset of ventricular diastole so that the atrial blanking period 436 may include both the A1 and A2 events. In this way an A1 or A2 event is not falsely sensed as the A4 event. An A3 window 424 may be set having a starting time 420 corresponding to the end of the post-ventricular atrial blanking period 436 and an ending time 422. The ending time 422 may also be considered a starting time of an A4 sensing window 450, though A4 signals may be sensed during the A3 window in some instances.

A4 events 408 and 418 may be detected based on a multi-level A4 sensing threshold 444. As seen by the lower motion sensor signal 410, the A4 event 418 may occur earlier after the A3 window 424 due to changes in atrial rate or differences in the atrial and ventricular rate during asynchronous ventricular pacing. In some instances, as the atrial rate increases, the A4 event 418 may occur within the A3 window 424. When this occurs, the A3 event 416 and the A4 event 418 may fuse as passive and active ventricular filling occur together. The fused A3/A4 event may have a high amplitude, even greater than the amplitude of either the A3 event 416 or the A4 event 418 when they occur separately. As such, in some examples a first, higher A4 sensing threshold amplitude 446 may be established and applied to the motion sensor signal for detecting an early A4 signal that is fused with the A3 signal during the A3 window 424. A second, lower A4 sensing threshold amplitude 448 may be established and applied to the motion sensor signal for detecting relatively later A4 signals, after the ending time 422 of the A3 window 424, during an A4 window 450. The A4 window 450 extends from the ending time 422 of the A3 window 424 until an A4 event is detected or until the next ventricular electrical event, sensed or paced, whichever comes first. The earliest crossing of the A4 sensing threshold 444 by the motion sensor signal after the starting time 420 of the A3 window (or after the expiration of the atrial blanking period 436) may be detected as the A4 event. Techniques for establishing and adjusting an early A4 sensing threshold amplitude 446 used during the A3 window 424 and a late A4 sensing threshold amplitude 448 used after the ending time 422 of the A3 window 424, during the A4 window 450, are described in the above incorporated U.S. Patent Application Publication No. 2020/0179707 (Splett, et al.), U.S. Patent Application Publication No. 2020/0179708 (Splett, et al.), U.S. Patent Application Publication No. 2021/0236825 (Sheldon, et al.) and in U.S. Patent Application Publication No. 2021/0236826 (Sheldon, et al.).

Figure 7:
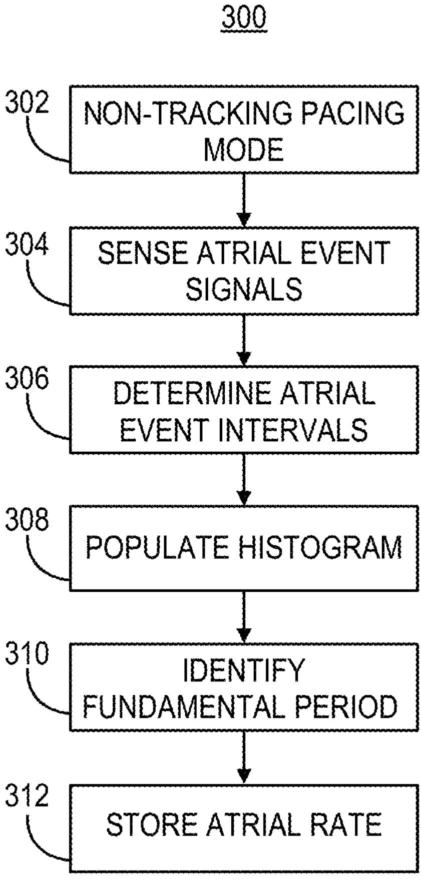
FIG. 7 is a flow chart of a method for determining an atrial rate from a motion sensor signal according to some examples.

FIG. 7 is a flow chart 300 of a method for determining an atrial rate from a motion sensor signal according to some examples. At block 302, control circuit 206 operates in a non-atrial tracking ventricular pacing mode. The pacing mode may be set to the non-atrial tracking pacing mode upon implantation of pacemaker 14, e.g., during a set up procedure for establishing atrial sensing control parameters. In other instances, the pacing mode may be switched from an atrial synchronous pacing mode to a non-atrial tracking pacing mode on a scheduled basis for determining the atrial rate, re-establishing atrial sensing control parameters, performing a pacing capture threshold test, other reasons. The pacing mode may be switched from an atrial synchronous pacing mode to the non-atrial tracking pacing mode in response to pacing mode switching criteria being met according to programmed pacing therapies implement in pacemaker 14. During the non-atrial tracking or "asynchronous" ventricular pacing mode, control circuit 206 may set ventricular pacing escape intervals to a predetermined pacing rate, e.g., 40, 50 or 60 pulses per minute, for controlling pulse generator 202 to deliver the asynchronous pacing pulses at a fixed rate (in the absence of sensed ventricular event signals).

At block 304, control circuit 206 senses atrial event signals from the motion signal received from motion sensor 212. In some examples, for the purposes of determining an atrial rate, the atrial event signals may be sensed by atrial event detector circuit 240 only after expiration of the A3 window in response to the motion signal crossing an A4 sensing threshold. In other examples, atrial event detector circuit 240 may sense the atrial event signal during the A3 window or during the A4 window, in response to the motion signal crossing an early, higher A4 sensing threshold amplitude during the A3 window or a later, lower A4 sensing threshold amplitude during the A4 window, whichever occurs first.

At block 306, control circuit 206 determines atrial event intervals. Each atrial event interval is the time interval between two consecutively sensed atrial event signals. One, none or more than one ventricular pacing pulse (and/or sensed R-wave) may occur during each atrial event interval because the ventricular rate may be different than the atrial rate, the ventricular pacing rate is asynchronous with the atrial rate, and in some ventricular cycles the atrial event may occur during the post-ventricular atrial blanking period (or during the A3 window and not used for atrial rate determination at least in some examples).

Control circuit 206 may store the atrial event intervals in memory 210 at block 308. Control circuit 206 may store the atrial event intervals in memory 210 in the form of a histogram by counting or logging the number of atrial event intervals that occur in each of a plurality of histogram bins allocated to respective atrial event interval ranges. In this way, a frequency distribution of the atrial event intervals determined at block 306 may be stored in memory 210.

At block 310, control circuit 206 may determine the fundamental period of the stored atrial event intervals. As described below, control circuit 206 may determine a best fit of the atrial event interval data by determining a best fit harmonic relationship of the atrial event intervals assuming that peaks in the frequency distribution are harmonically related to the fundamental period of the atrial event intervals. For example, the atrial rate interval can be determined from the best fit relationship when the harmonic equals 1. The atrial rate (or corresponding rate interval) may be determined based on the fundamental period and stored in memory 210 at block 312. As described below, control circuit 206 may use the atrial rate for determining or adjusting one or more atrial event sensing control parameters or other control parameters used by pacemaker 14 in sensing cardiac signals and/or delivering ventricular pacing pulses. In some examples, the atrial rate may be used to verify ventricular tracking of the atrial rate after switching back to an atrial synchronous ventricular pacing mode. When ventricular rate is not tracking at the expected atrial rate determined from the atrial event intervals, one or more atrial event sensing control parameters may be adjusted. In other examples, the atrial rate may be used to set a limit or range of one or more atrial sensing control parameters, such as the maximum and/or minimum A3 window ending time (e.g., A3 window ending time 422 shown in FIG. 6).

Each atrial event interval determined at block 306 may or may not be equal to a true atrial event interval because some true atrial event signals will not be sensed, e.g., during the post-ventricular atrial blanking period. As described below, an atrial event interval may be about equal to the first harmonic of the atrial rate interval, a second harmonic of the atrial rate interval, a third harmonic of the atrial rate interval, or an even higher harmonic depending on the relative timing of a sensed atrial event signal since a preceding sensed atrial event signal. None, one, two or more true atrial events (that go unsensed) may occur between two consecutively sensed atrial event signals during asynchronous ventricular pacing because some atrial event signals may be unsensed due to their timing during the ventricular cycle. As such, it is noted that the "atrial rate interval" as used herein refers to the time interval that occurs between atrial events if they are occurring at the determined atrial rate. The "atrial event intervals" determined at block 306 are time intervals that are determined by control circuit 206 between two consecutively sensed atrial event signals, which may or may not be at the atrial rate interval. Using the techniques disclosed herein, the atrial rate interval and corresponding atrial rate may be determined even when none of the atrial event signals are sensed at a true atrial event interval, e.g., when all atrial event intervals include one or more intervening unsensed atrial events.

The atrial rate determined at block 310 by identifying a first harmonic of the atrial event intervals may be a sinus rate arising from the SA node. In other instances, the atrial rate may be a paced atrial rate when the atria are being paced, e.g., by another pacemaker implanted in the patient. In some instances, the atrial rate may be a rate of any combination of paced atrial events and/or intrinsic atrial events, which may include sinus and/or non-sinus depolarizations of the atria. In some cases, an atrial event interval may be determined between atrial events that include a non-sinus atrial event, e.g., a premature atrial contraction or a non-sinus atrial tachycardia beat. However, during atrial fibrillation or atrial flutter, the atrial event signal of the motion signal may not be sensed because it may have a relatively low amplitude compared to paced or sinus atrial beats.

Figure 8:
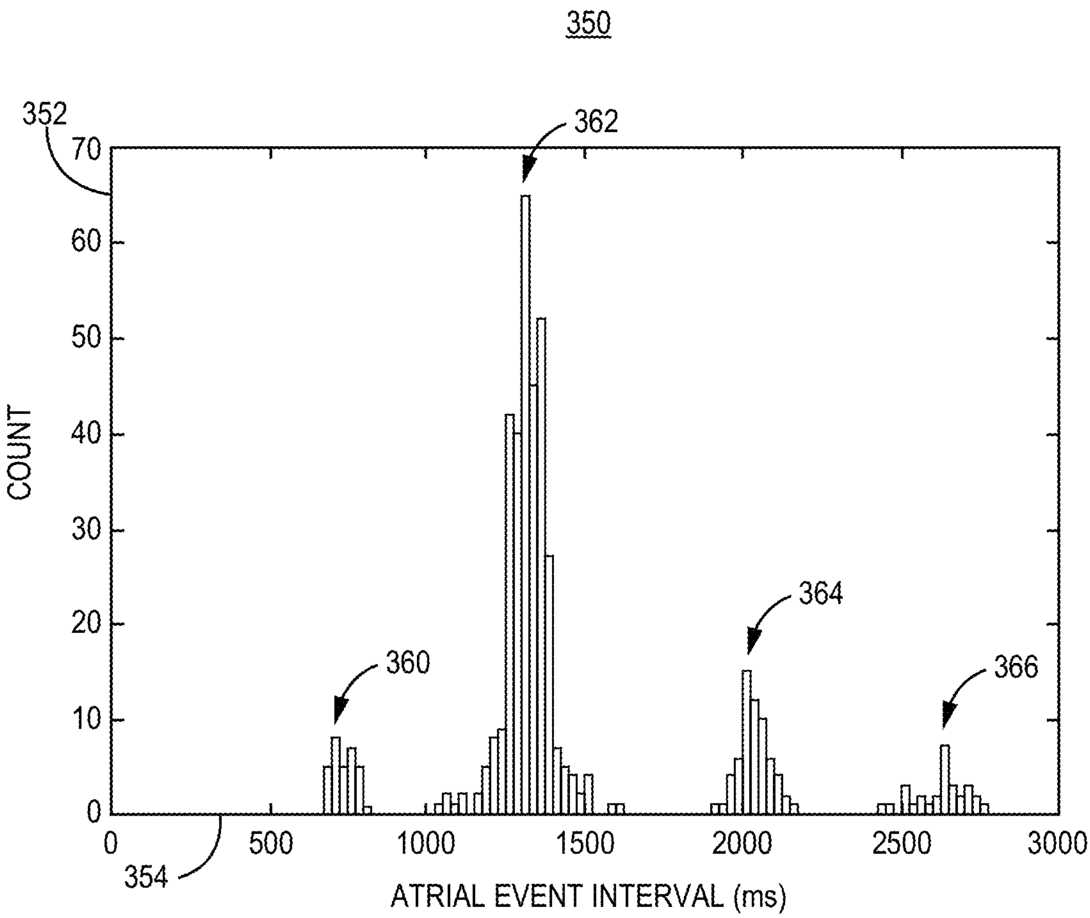
FIG. 8 is a diagram of a frequency distribution plot of atrial event intervals determined by a medical device and stored in a histogram in the medical device memory according to one example.

FIG. 8 is a diagram 350 of a frequency distribution plot of atrial event intervals determined by control circuit 206 and stored in a histogram in memory 210 according to one example. Atrial event intervals are plotted on the x-axis 354 in milliseconds (ms). Atrial event interval bins may be allocated in memory 210 to count the number of atrial event intervals occurring in each bin range. The total range of the atrial event interval bins may range from 300 ms to 8,000 ms or from 400 ms to 6,000 ms, as examples, and the individual bin widths may be 10 to 50 ms, as examples. The narrower the range of the individual bin widths the higher the resolution of the atrial rate determination. The count or frequency of atrial event intervals occurring in each atrial event interval bin range is plotted on the y-axis 352.

The frequency distribution plot is observed to include multiple distinct peaks 360, 362, 364 and 366 associated with groupings of atrial event interval occurrences. The groupings of atrial event interval occurrences around distinct peaks 360, 362, 364 and 366 may be separated from each other by one or more atrial event interval bins having a zero count in some instances. In the example of FIG. 8, most atrial event intervals occur in the grouping of histogram bins surrounding the second peak 362, with the highest count of atrial event intervals at approximately 1.325 seconds. Other atrial event intervals occur with significant frequency at about 700 ms (first peak 360), about 2,000 ms (third peak 364) and about 2,700 ms (fourth peak 366). The peaks 360, 362, 364 and 366 may be assumed to be harmonically related with one peak being the first harmonic corresponding to the fundamental period or, in some cases, being the second harmonic corresponding to double the fundamental period (e.g., when shortest atrial event intervals determined include one or more intervening, unsensed atrial event signal).

Control circuit 206 may identify groups of occupied atrial event histogram bins surrounding each local peak 360, 362, 364 and 366 of the frequency distribution. Control circuit 206 may determine an atrial event interval representative of each frequency distribution peak 360, 362, 364, and 366. For example, control circuit 206 may determine the atrial event interval that occurs most frequently (e.g., the most populated histogram bin) within each grouping of occupied bins associated with a local peak of the frequency distribution. In other examples, control circuit 206 may determine the average or median atrial event interval within each grouping of occupied bins surrounding and including a given peak. In still other examples, control circuit 206 may determine an atrial event interval corresponding to a peak of a Gaussian fit of the occupied atrial event interval bins surrounding and including a given local peak of the frequency distribution. The representative atrial event intervals may be harmonically related to the atrial event interval corresponding to the true atrial rate. Control circuit 206 may therefore determine an estimate of the true atrial rate based on the determined representative atrial event intervals that can be harmonically related to the true atrial rate interval.

Figure 9:
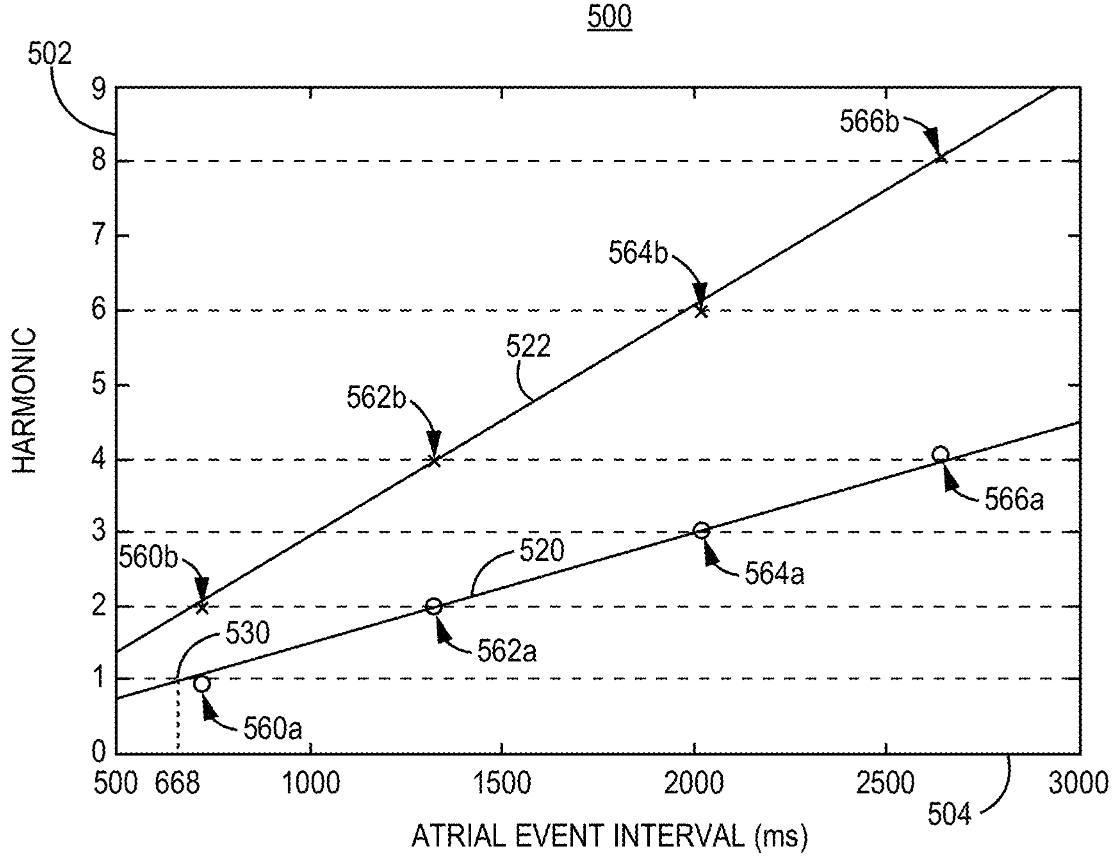
FIG. 9 is a graph of representative atrial event intervals determined from the frequency distribution of the atrial event intervals shown in FIG. 8.

FIG. 9 is a graph 500 of representative atrial event intervals determined from the frequency distribution of the atrial event intervals shown in FIG. 8. Harmonics are plotted along the y-axis 502 as a function of the representative atrial event intervals plotted along the x-axis 504. The representative atrial event interval 560 (plotted twice as 560*a* and 560*b*) is determined from the first group of occupied atrial event interval bins surrounding and including the first peak 360 of the histogram shown in FIG. 8. The representative atrial event interval 562 (plotted twice as 562*a* and 562*b*) is determined from the second group of atrial event interval bins of the second peak 362. The representative atrial event interval 564 (plotted twice as 564*a* and 564*b*) is determined from the third group of occupied atrial event interval bins of the third peak 364. The atrial event interval 566 (plotted twice as 566*a* and 566*b*) is determined from the fourth group of atrial event intervals of the fourth peak 366. Control circuit 206 may be configured to determine a best fit model, e.g., using a least squares method, of the representative atrial event intervals 560, 562, 564 and 566 assuming they are harmonically related. Based on the best fit model of the representative atrial event intervals 560, 562, 564 and 566 plotted in harmonic relation, control circuit 206 may determine the atrial rate.

The representative atrial event intervals determined for each peak 360, 362, 364 and 366 of the frequency distribution shown in FIG. 8 are plotted as circles 560*a*, 562*a*, 564*a*, and 566*a* in FIG. 8 assuming that the first representative atrial event interval 560*a* is associated with the first harmonic of the true atrial rate interval. The representative atrial event interval 562*b* corresponding to the second peak 362 in FIG. 8 is plotted as being the second harmonic. The third and fourth representative atrial event intervals 564*a* and 566*a* determined from the groups of atrial event intervals around and including the third and fourth peaks 364 and 366, respectively, are plotted as the third and fourth harmonics. A best fit model 520 may be determined by control circuit 206 as a harmonic relationship of the atrial event intervals. According to the best fit model 520 defining the harmonic as a function of atrial event interval, the atrial rate interval 530 of 668 ms can be determined from the model when the harmonic is one. In this case, the best fit model 520 predicts an atrial rate interval of 668 ms, or an atrial rate of about 90 beats per minute (bpm). It is notable that the atrial rate interval 530 determined based on the best fit model of sensed atrial event intervals is not equal to an interval in the grouping of histogram bins associated with the highest peak 362 of the frequency distribution shown in FIG. 8. Most atrial event signals are being sensed at atrial event intervals that are about twice the true atrial rate interval in this example. The atrial events that are sensed are at about half the true atrial rate. Determination of the atrial rate as being equal to an average or median of atrial event intervals obtained during a non-atrial tracking ventricular pacing mode, therefore, may result in inaccurate atrial rate determination.

In some cases, for example when the atrial rate is high, the first peak of the atrial event intervals stored in the histogram as shown in FIG. 8 may occur at the second harmonic rather than the first harmonic of the atrial rate interval. As such, control circuit 206 may determine an alternative best fit model 522 of the representative atrial event intervals. Each of the representative event intervals associated with each peak are therefore plotted a second time in FIG. 9 for determining a second, alternative harmonic relationship of the atrial event intervals. The first representative atrial event interval 560*b* is plotted as the second harmonic for determining this alternative best fit model. Each subsequent representative atrial event interval 562*b*, 564*b* and 566*b* is plotted as the fourth, sixth and eighth harmonics, respectively, instead of the second, third and fourth as in the first best fit model 520. In the example shown, the atrial rate interval predicted by the alternative best fit model 522 at the first harmonic is less than 500 ms. The estimated atrial rate may be selected from the atrial rate interval predicted by the first best fit model 520 and the alternative atrial rate interval predicted by the alternative best fit model 522 based on whichever model 520 or 522 resulted in the best fit to the data. The model having the highest goodness of fit, e.g., based on the highest coefficient of determination (R-squared), smallest residuals or other goodness of fit measure, may be selected for determining the atrial rate. In the example shown, the first best fit model 520, that assumes the first peak of the frequency distribution corresponds to the first harmonic of the atrial rate, is determined to have a better goodness of fit than the alternative best fit model 522 based on the R-squared values of each model. The atrial rate interval 530 can therefore be determined from the first model 520 as being 668 ms.

In some examples, upper and/or lower limits to the atrial rate may be set to avoid determining a non-physiological atrial rate based on the harmonic relationship. For example, the atrial rate may be required to be less than 150 bpm, less than 180 bpm, less than 200 bpm or less than 300 bpm and/or greater than 20 bpm or greater than 30 bpm. When a best fit model predicts an atrial rate outside an upper or lower physiological limit, another best fit model of the harmonic relationship of atrial event intervals that assigns a different harmonic to the first and subsequent peaks of the atrial event interval frequency distribution may be used to determine the atrial rate.

In other examples, the best fit model selected for determining the atrial rate interval when the harmonic equals 1 may be selected by control circuit 206 based at least in part on an A2 event interval, also referred to herein as a "systolic event time interval." As described above in conjunction with FIGS. 5 and 6, the A2 event signal is expected to follow the A1 event or a ventricular electrical event such as a ventricular pacing pulse or an intrinsic R-wave at a consistent interval because the A2 event signal corresponds to the end of systole. The systolic time interval from the onset to the end of ventricular systole can shorten with higher sympathetic tone, which is also associated with faster atrial sinus rates. As such, the time interval from the A1 event to the A2 event in the acceleration signal or the time interval from a ventricular electrical event (ventricular pacing pulse or sensed R-wave) to the A2 event signal may be determined by control circuit 206 as the A2 event interval. Control circuit 206 may be configured to compare the A2 event interval to a threshold interval for indicating a relatively higher sympathetic tone and faster sinus rate or a relatively lower sympathetic tone and slower sinus rate. The threshold interval may be a baseline interval established by control circuit 206 by determining the A2 event interval at pacemaker implant or during a patient follow-up or during a known resting state of the patient for example. The threshold interval may be a default or nominal threshold, e.g., set based on empirical data, or may be programmable by a user based on determination of the A2 event interval during a known atrial rate of the patient, e.g., a known resting rate.

When the A2 event interval is shorter than the threshold interval, control circuit 206 may select a best fit model that plots the representative atrial event interval associated with the first peak of the atrial event interval frequency distribution as the second harmonic instead of the first harmonic. When the atrial rate is relatively fast, e.g., faster than 80 bpm, 90 bpm or 100 bpm, atrial event intervals have a higher likelihood of being a second or third harmonic of the true atrial rate interval than when the atrial rate is relatively slow. When the A2 event interval is relatively long, associated with slower atrial sinus rates, control circuit 206 may select the best fit model that plots the representative atrial event interval associated with the first peak of the atrial event interval frequency distribution as the first harmonic. When the atrial rate is relatively slow, atrial event intervals determined during asynchronous ventricular pacing have a higher likelihood of being at the true atrial rate interval than when the atrial rate is relatively faster.

While the techniques disclosed in conjunction with FIG. 9 and other flow charts and diagrams presented herein are described as being performed by control circuit 206, it is to be understood that atrial event intervals determined by control circuit 206 may be analyzed by another processor, e.g., external device processor 20, for determining a best fit model and an atrial rate interval predicted by the best fit model. The atrial event intervals determined by control circuit 206 may be transmitted from pacemaker 14 to external device 20 via telemetry circuit 208. External device processor 52 may determine the harmonic relationships of the atrial event intervals and determine a best fit model having the highest R-squared (or other goodness of fit measure). External device processor 52 may determine the atrial rate interval when the harmonic is 1 from the best fit model having the highest goodness of fit and transmit the determined atrial rate interval back to pacemaker 14.

Figure 10:
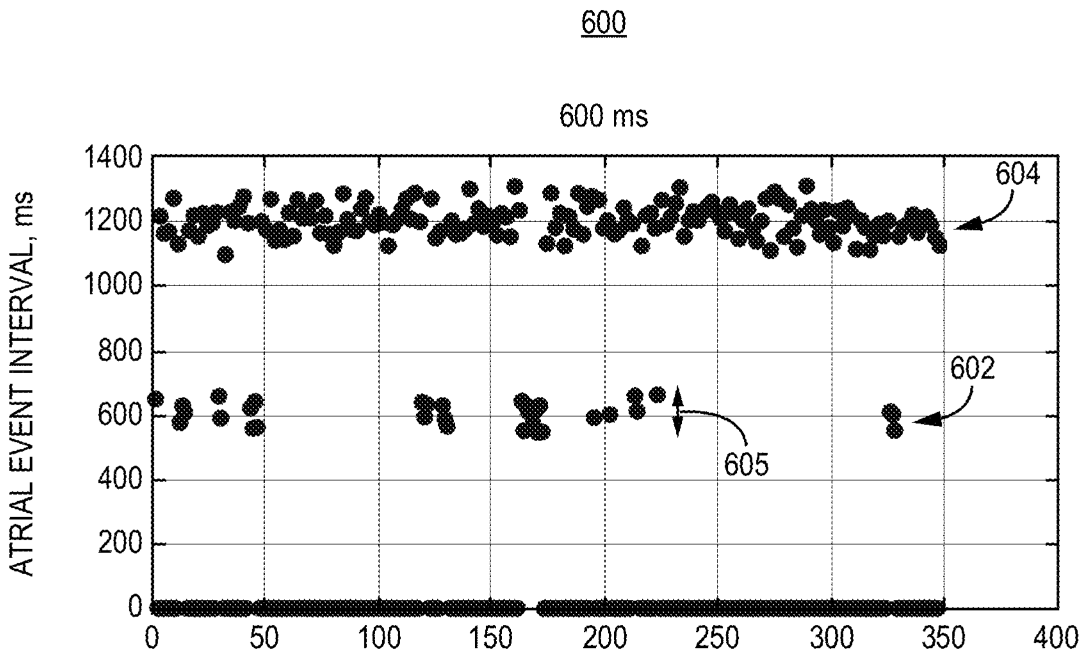
FIG. 10 is a diagram of plots of the atrial event intervals that may be determined by a pacemaker during an asynchronous ventricular pacing mode and used for determining the atrial rate.
Figure 10:
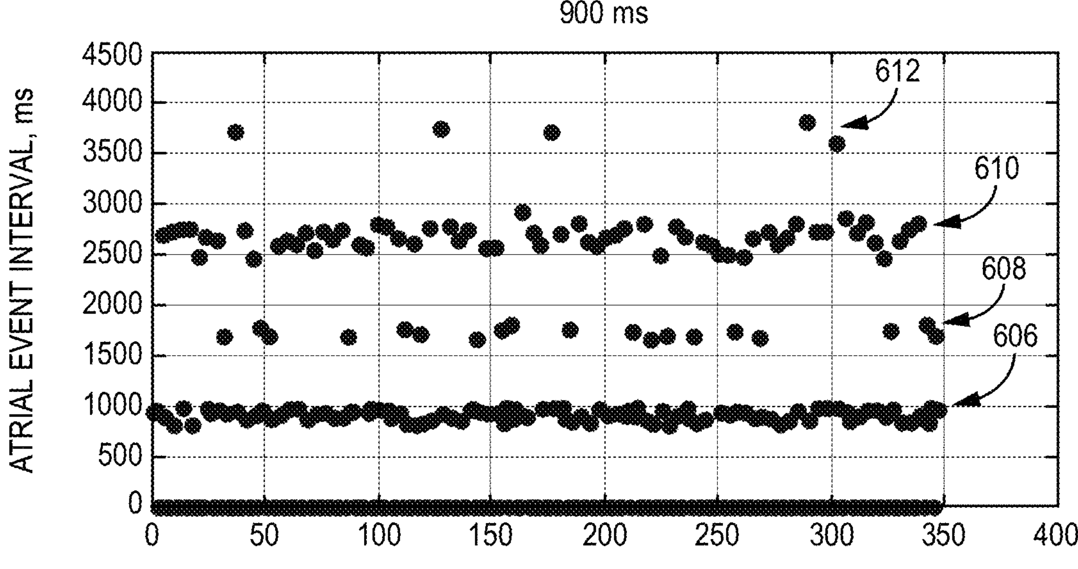

FIG. 10 is a diagram of plots of the atrial event intervals that may be determined by control circuit 206 during an asynchronous ventricular pacing mode and used for determining the atrial rate. The atrial event intervals are shown in ms along the y-axis in both plots. The ventricular cycle number is plotted along the x-axis in both plots. Each ventricular cycle starts with a non-atrial tracking ventricular pacing pulse, e.g., delivered at a pacing rate of 50 pulses per minute (ventricular cycle length of 1200 ms). Each ventricular cycle includes an A3 window and, if the high A4 sensing threshold amplitude is not crossed by the acceleration signal during the A3 window, an A4 window as described above in conjunction with FIG. 6.

The A3 window may begin 500 to 600 ms after the ventricular pacing pulse, e.g., at 550 ms, and end 750 to 1000 ms, e.g., at 900 ms, after the ventricular pacing pulse. The A4 window begins upon expiration of the A3 window and ends upon sensing an atrial event or upon the next ventricular pacing pulse (at 1200 ms in this example of 50 pulses per minute pacing rate) when an atrial event is not sensed. The A4 window can extend from 900 ms to 1200 ms, for example. In some ventricular cycles, the acceleration signal does not cross either the high A4 sensing threshold during the A3 window or the low A4 sensing threshold during the A4 window. The atrial event may occur during the post ventricular atrial blanking period. Therefore each plot in FIG. 10 includes ventricular cycles associated with an atrial event interval of 0 (no atrial event sensed during the associated ventricular cycle); however these cycles can be ignored for the purposes of determining a harmonic relationship of the atrial event intervals.

In the upper plot, the true atrial rate is 100 bpm corresponding to an atrial rate interval of 600 ms. Some atrial events are sensed at atrial event intervals 602 of about 600 ms, corresponding to a first harmonic of the atrial rate. When stored in a histogram and plotted in a frequency distribution, a first peak of the frequency distribution will occur at about 600 ms, the first harmonic of the atrial rate. A second peak of the frequency distribution will occur at around 1200 ms due to atrial event intervals 604 occurring at the second harmonic of the atrial rate.

In the lower plot, the true atrial rate is 67 bpm corresponding to an atrial rate interval of 900 ms. A relatively higher occurrence of atrial event intervals 606 is observed at about the first harmonic of the atrial rate (about 900 ms) in the lower plot than the occurrence of atrial event interval 602 at about the first harmonic of the atrial rate in the upper plot. In the lower plot, atrial event intervals 608 occur at about the second harmonic, approximately 1800 ms. Atrial event intervals 610 occur at about the third harmonic, around 2700 ms in this example. A few atrial event intervals 612 occur at about the fourth harmonic, or about 3600 ms, in the lower plot.

As seen by the upper and lower plots of FIG. 10, the most highly occupied histogram bins corresponding to a given peak of the frequency distribution may or may not be about equal to the first harmonic of the atrial rate. In the upper plot, the atrial event intervals 604 stored in histogram bins in memory 210 correspond to the second harmonic of the atrial rate and form the highest peak in the frequency distribution. In the lower plot, the atrial event intervals 606 stored in histogram bins in memory 210 correspond to the first harmonic of the atrial rate and form the highest peak in the frequency distribution. Accordingly, the most frequently occurring atrial event intervals do not necessarily equate to the atrial rate interval and may, as shown in the upper plot of FIG. 10, represent a higher harmonic of the atrial rate.

As such, a best fit model can be selected from multiple harmonic relationships of the atrial event intervals by control circuit 206 for determining the atrial rate interval at block 310 of FIG. 7. When two different best fit models are determined, as shown in FIG. 9, the best fit model used to determine the atrial rate when the harmonic is one may be selected by control circuit 206 based on a goodness of fit measurement, based on an A2 time interval, based on a previously known atrial rate for the patient (which may be entered by a clinician interacting with external device 20) and/or based on the determined atrial rate being within predetermined physiological limits in various examples.

In some instances, the high A4 sensing threshold applied to the acceleration signal during the A3 window may be too low resulting in oversensing of A3 event signals as false atrial event signals. In this situation, the determined atrial rate could match the asynchronous ventricular paced rate. Control circuit 206 may be configured to compare the determined atrial rate to the non-atrial tracking ventricular pacing rate. If the atrial rate matches the non-atrial tracking ventricular paced rate (e.g., if the atrial rate interval matches the ventricular pacing rate interval within a threshold range of the ventricular pacing rate interval), control circuit 206 may adjust the non-atrial tracking ventricular pacing rate and re-determine the atrial rate. If the atrial rate changes to the adjusted ventricular pacing rate, control circuit 206 may increase the high A4 sensing threshold amplitude, change to using atrial event signals sensed only during the A4 window for determining atrial event intervals, and/or increase the A3 window ending time. The atrial rate determination may be repeated during the non-atrial tracking ventricular pacing mode after adjusting the atrial event sensing parameters to avoid oversensing of A3 event signals.

In other examples, control circuit 206 may be configured to determine a metric of variability of the atrial event intervals when the determined atrial rate matches the non-atrial tracking ventricular pacing rate. When A3 events are oversensed during ventricular pacing at a fixed rate, the variation of the atrial event intervals is small compared to normal sinus rhythm variation of true atrial event intervals. At a given harmonic of the ventricular paced rate, the atrial event intervals determined from oversensed A3 event signals will have a small variability. In the upper plot of FIG. 10, the range 605 of atrial event intervals 602 is approximately 150 ms. In contrast, the atrial event intervals determined from oversensed A3 event signals during asynchronous ventricular pacing may be consistently equal to the ventricular pacing rate interval (e.g., within a small margin of error) and may largely if not exclusively occur at the first harmonic equal to the ventricular pacing interval. As such, control circuit 206 may determine a metric of atrial event interval variability when the determined atrial rate matches the non-atrial tracking paced ventricular rate. If A3 oversensing is determined based on the analysis of atrial event interval variability or based on the determined atrial rate changing with changes in ventricular pacing rate, control circuit 206 may adjust one or more control parameters used to sense atrial events during the non-atrial tracking ventricular pacing mode or use only atrial event signals sensed during the A4 window.

Figure 11:
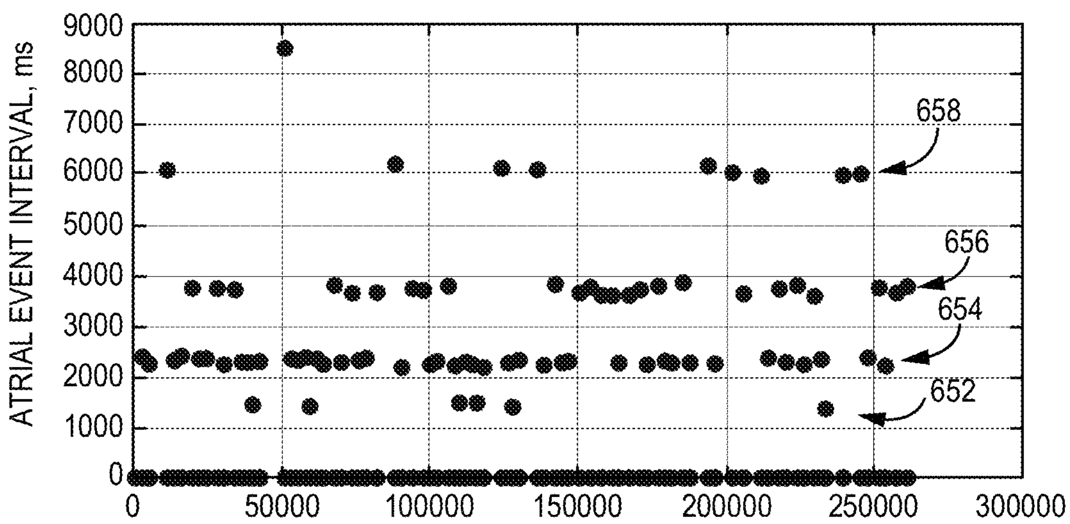
FIG. 11 is a diagram of plots of atrial event intervals that may be determined by a pacemaker during an asynchronous ventricular pacing mode for determining the atrial rate according to other examples.
Figure 11:
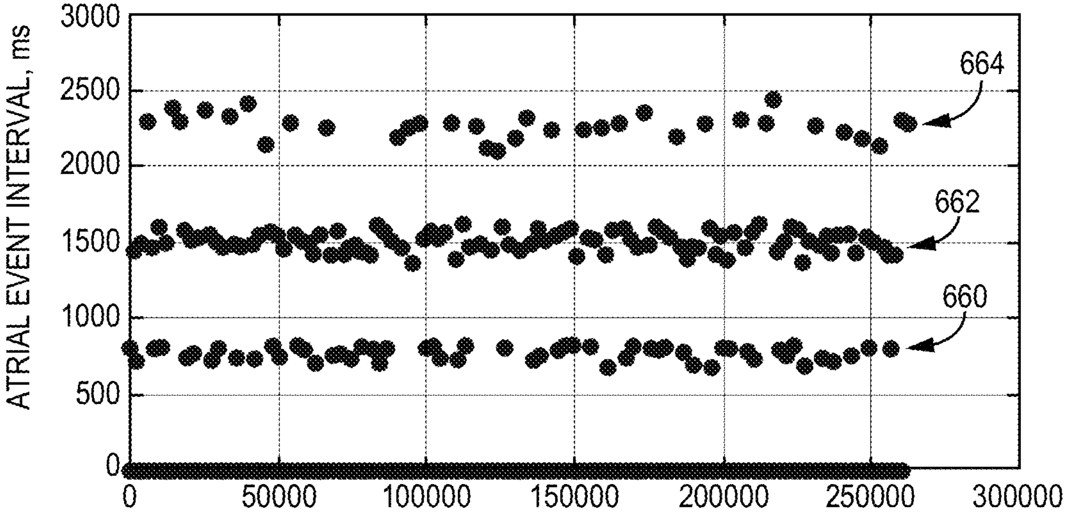

FIG. 11 is a diagram 650 of plots of atrial event intervals that may be determined by control circuit 206 during an asynchronous ventricular pacing mode for determining the atrial rate according to other examples. In FIG. 11, the ventricular cycle number is plotted along the x-axis in both of the upper and lower plots and the corresponding atrial event interval is plotted along the y-axis. The ventricular cycles are paced ventricular cycles with the asynchronous pacing rate set to 50 pulses per minute. In both the upper and lower plots, the atrial rate is 80 bpm, corresponding to an atrial rate interval of 750 ms.

In the upper plot of FIG. 11, atrial event signals sensed only in the A4 window of a given ventricular cycle are used for determining the atrial event intervals. The A4 window in this example begins at 900 ms after the ventricular pacing pulse and extends up to 1200 ms, when the next ventricular pacing pulse is delivered. The total time window duration during each ventricular cycle from which sensed atrial event signals are used for determining atrial event intervals is therefore up to 300 ms long in this example. Atrial event signals sensed during the A3 window are ignored for determining atrial event intervals in this example. A nominal low A4 sensing threshold amplitude of 1.0 to 1.8 $m/s^2$ or about 1.5 $m/s^2$ may be applied during the A4 window for sensing atrial event signals.

In the lower plot of FIG. 11, an atrial event signal sensed in either the A3 window or the A4 window of a given ventricular cycle is used for determining an atrial event interval. The nominal low A4 sensing threshold amplitude of 1.5 $m/s^2$ may be applied during the A4 window for sensing atrial event signals, and a nominal high A4 sensing threshold amplitude of 3.0 to 4.0 $m/s^2$ may be applied during the A3 window for sensing atrial event signals, as non-limiting examples. The A3 window extends from 550 ms up to 900 ms after each ventricular pacing pulse. The total time window during each ventricular cycle during which atrial event signals can be sensed for use in determining atrial event intervals is therefore up to 650 ms long in this example.

In the upper plot, during an atrial rate of 80 bpm, no atrial event intervals are recorded at the first harmonic of the atrial rate, around 750 ms, when only the A4 window atrial event signals are used for populating the atrial event histogram. The shortest atrial event intervals 652 are observed to occur at the second harmonic of the atrial rate, around 1500 ms, when atrial event signals sensed only in the A4 window are used for populating the atrial event interval histogram. The histogram bins around the second harmonic of 1500 ms are relatively sparsely populated for the data shown in the upper plot. The highest peak of the frequency distribution of atrial event intervals occurs around the third harmonic of the atrial rate as observed by the higher occurrence of atrial event intervals 654 at about 2,250 ms. No atrial event intervals are recorded at the fourth harmonic of the atrial rate, around 3,000 ms. Atrial event intervals 656 are recorded at about the fifth harmonic, around 3,750 ms. Some atrial event intervals 658 are observed around the eighth harmonic, at about 6,000 ms in this example. As observed in the upper plot of FIG. 11, when the total time window during which sensed atrial event signals can be used for determining atrial event intervals is relatively short (only the A4 window in this case), relatively higher harmonics are represented by the populated atrial event interval histogram.

When the atrial event signals sensed in the A3 window and the A4 window are used for determining atrial event signals, however, as shown by the lower plot in FIG. 11, the atrial event intervals 660 around the first harmonic of the atrial rate (about 750 ms) occur relatively frequently. Atrial event intervals 662 around the second harmonic of the atrial rate (about 1500 ms) occur with the greatest frequency. Atrial event intervals 664 around the third harmonic of 2,250 ms also occur with relatively high frequency. As observed in the lower plot, when the total time window during which sensed atrial event signals can be used for determining atrial event intervals is relatively long (up to 650 ms in this example of including both the A3 and A4 windows), relatively lower harmonics may be represented by the populated atrial event interval histogram with greater frequency than when a shorter total time window of sensed atrial event signals is used.

As shown by the plots of FIG. 11, the atrial event intervals occurring with the highest frequency do not necessarily equate to the atrial rate interval. Furthermore, the harmonics at which the atrial event intervals occur with the greatest frequency may depend at least in part on the duration of the total time window during from which sensed atrial event signals can be used for determining atrial event intervals. For instance, when atrial event signals sensed only during the A4 window are used, as represented by the upper plot, no atrial event intervals are recorded at the first harmonic of the atrial rate. When the total time window during which sensed atrial event signals are utilized for determining atrial event intervals is increased to include the A3 window and the A4 window, as represented by the lower plot, atrial event intervals 660 occur at the first harmonic of the atrial rate with relatively high frequency.

Accordingly, at block 310 of FIG. 7, control circuit 206 may identify the fundamental period of the atrial rate by using a best fit model that sets the representative atrial event interval corresponding to the first peak of the frequency distribution to a harmonic greater than one when a relatively short total time window, e.g., only the A4 window, is used for acquiring atrial event signals that are utilized for determining atrial event intervals. When the duration of the total time window from which sensed atrial event signals can be utilized for determining atrial event intervals is relatively longer, e.g., both the A3 window and the A4 window, control circuit 206 may select a best fit model that plots the representative atrial event interval of the first peak of the frequency distribution as the first harmonic.

In some examples, if the atrial event interval histogram is too sparsely populated to generate a best fit model with a high goodness of fit, e.g., less than a threshold number of atrial event intervals are accumulated and stored in the histogram, control circuit 206 may increase the total time window during which sensed atrial event signals can be utilized for determining atrial event intervals. For instance, the total time window may be increased from being only the A4 window to including both the A3 window and the A4 window sensed atrial event signals when fewer than a threshold number of atrial event intervals occupy the histogram bins after a data acquisition period. For example, if less than 30, less than 40, less than 50, less than 100 (or less than any other selected threshold number of) atrial event intervals are accumulated after one minute, two minutes (or any other time duration) of data acquisition, control circuit 206 may increase the total time window within a ventricular cycle during which sensed atrial event signals can be acquired and used for determining atrial event intervals. Control circuit 206 may continue acquiring atrial event intervals using the increased time window, e.g., the A3 window and the A4 window, for sensing atrial event signals. In other examples, control circuit 206 may continue to use only the A4 window sensed atrial event signals but increase the total time window by shortening the A3 window ending time and/or decreasing the ventricular pacing rate to enable sensing of A4 event signals during a longer A4 window.

In still other examples, in response to a sparsely populated histogram, control circuit 206 may extend the number of ventricular cycles or total time over which atrial event intervals are acquired for populating the atrial event interval histogram. In still other examples, when the atrial event signals sensed during the A3 window are utilized, the high A4 sensing threshold amplitude may be reduced if the atrial event interval histogram is sparsely populated, particularly in the range of atrial event interval histogram bins that are expected to include a first harmonic of the atrial rate such as histogram bins in the range between 500 ms and 1500 ms. When the atrial event signals sensed during only the A4 window are utilized, the low A4 sensing threshold amplitude may be reduced if the atrial event interval histogram is sparsely populated, particularly in the range of atrial event interval histogram bins that are expected to include a first harmonic and/or second harmonic of the atrial rate such as histogram bins in the range between 500 ms and 3000 ms.

Control circuit 206 may therefore increase the total time window during each ventricular cycle during which sensed atrial event signals can be utilized for determining atrial event intervals (e.g., by shortening the A3 window ending time, decreasing the ventricular pacing rate, and/or by utilizing atrial event signals sensed during both the A3 windows and the A4 windows), adjust the high and/or low A4 sensing threshold amplitude, and/or increase a total data acquisition time period over which atrial event intervals are determined and stored in memory 210 to promote densely populated histogram bins over a range of atrial rate harmonics. One or more best fit models of the accumulated atrial event intervals may be determined from harmonic relationships of the atrial event intervals, e.g., at least two harmonic relationships as described in conjunction with FIG. 9. An atrial rate can be determined by control circuit 206 from a selected best fit model of a harmonic relationship of the atrial event intervals when the harmonic is equal to one in the selected best fit model.

In some examples, control circuit 206 may generate two histograms of atrial event intervals; one histogram generated from only A4 window atrial event signals (e.g., as represented by the upper plot of FIG. 11) and another histogram generated from both A3 and A4 window atrial event signals (e.g., as represented by the lower plot of FIG. 11). One or more best fit models may be determined from each of the histograms based on one or more harmonic relationships of the atrial event intervals for estimating the atrial rate. The atrial rate may be determined from one of the best fit models having the highest goodness of fit and/or selected based on other criteria as described above, such as physiological upper and/or lower limits. In some examples, control circuit 206 may determine the atrial rate based on an agreement between the atrial rate determined from a best fit model generated from atrial event intervals acquired using only the A4 window atrial event signals and from a best fit model generated from atrial event intervals acquired using both of the A3 and A4 window atrial event signals.

Figure 12:
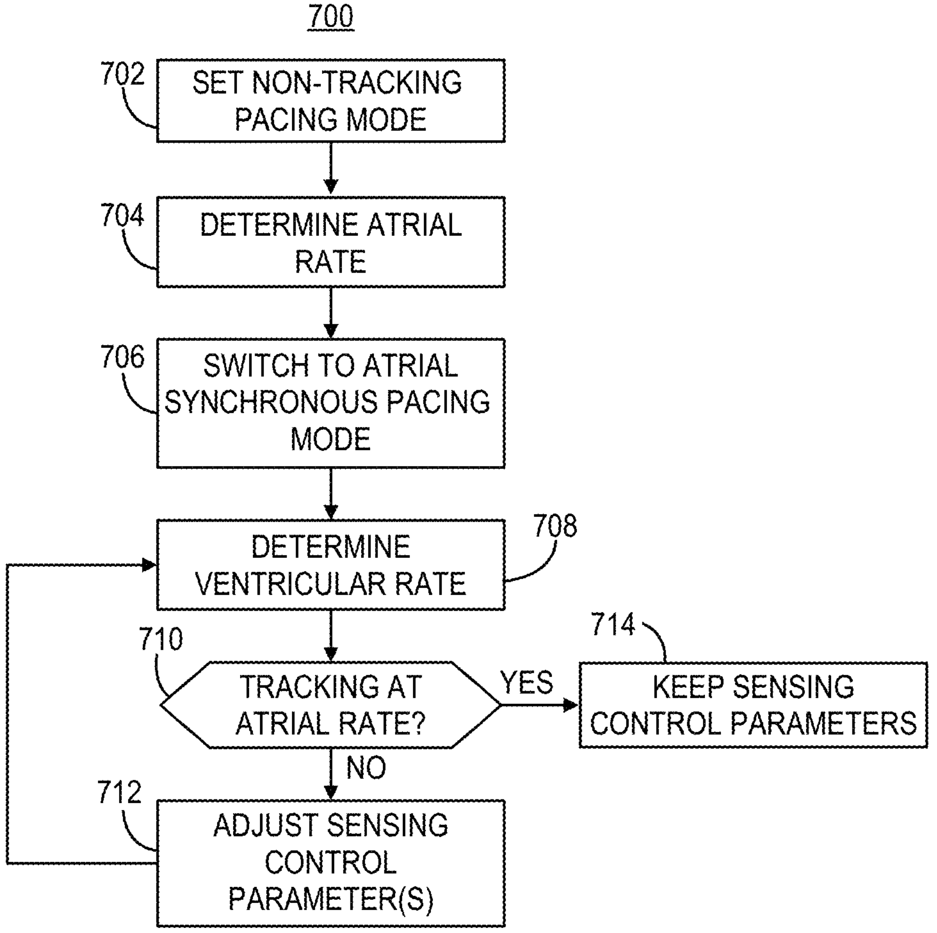
FIG. 12 is a flow chart of a method for controlling the settings of a control parameter used in delivering atrial synchronous ventricular pacing according to some examples.

FIG. 12 is a flow chart 700 of a method for controlling the settings of a control parameter used in delivering atrial synchronous ventricular pacing according to some examples. In this instance, flow chart 700 depicts a method for controlling the settings of an atrial event sensing control parameter based on a determined atrial rate. The atrial event sensing control parameter is used in sensing atrial event signals from the motion sensor signal by atrial event detector circuit 240, e.g., during an atrial synchronous ventricular pacing mode.

At block 702, control circuit 206 sets the pacing mode to a non-atrial tracking ventricular pacing mode, e.g., a VDI pacing mode. Pulse generator 202 may be controlled by control circuit 206 to deliver ventricular pacing pulses at a programmed lower rate or a nominal lower rate, e.g., 40, 50 or 60 pulses per minute. The process of flow chart 700 may be performed for determining atrial rate any time that the control circuit 206 is operating in a non-atrial tracking ventricular pacing mode for a time period that is long enough, e.g., at least one to two minutes, for control circuit 206 to acquire enough atrial event intervals, e.g., at least 20 to 30 atrial event intervals, to sufficiently populate the histogram for determining a best fit model as described above.

During the non-tracking pacing mode, control circuit 206 may determine the atrial rate using the techniques described above, e.g., in conjunction with FIGS. 7-11. Atrial event signals may be sensed by atrial event detector circuit 240 during the non-tracking pacing mode in response to A4 sensing threshold amplitude crossings that occur only during the A4 window in some examples. The A4 threshold amplitude during the A4 window may be set to a nominal, fixed value, e.g., 1.2 to 1.6 or about 1.5 $m/s^2$. In other examples, atrial event signals may be sensed in response to the earliest A4 sensing threshold amplitude crossing after expiration of the post-ventricular atrial blanking and refractory periods, which may be during the A3 window or the A4 window. A higher A4 sensing threshold amplitude may be applied during the A3 window than during the A4 window as described above in conjunction with FIG. 6 to avoid falsely sensing A3 event signals as atrial event signals. The higher A4 sensing threshold amplitude during the A3 window may be nominally set to 3.0 to 4.0 $m/s^2$.

At block 706, control circuit 206 switches to an atrial synchronous ventricular pacing mode, e.g., a VDD pacing mode. Pulse generator 202 is controlled by control circuit 206 to deliver ventricular pacing pulses at the expiration of AV pacing intervals, each started in response to atrial event detector circuit 240 sensing an atrial event signal from the motion sensor signal. At block 708, control circuit 206 determines a ventricular rate during the atrial synchronous ventricular pacing mode. The ventricular rate may be determined by determining ventricular event intervals between consecutive ventricular events, e.g., between consecutive ventricular pacing pulses and/or ventricular sensed event signals (e.g., R-sense signals as shown in FIG. 4). The ventricular event intervals may therefore include event intervals that begin and/or end with ventricular sensed event signals received from sensing circuit 204. However, since most patients receiving pacemaker 14 may have AV conduction block, the ventricular event intervals may consistently begin and end with ventricular pacing pulses delivered at the expiration of AV pacing intervals (and/or ventricular lower pacing rate intervals when an atrial event signal is not sensed).

Control circuit 206 may determine a representative ventricular event interval, e.g., a median or mean ventricular event interval from a series of ventricular event intervals, e.g., 3 to 30 ventricular event intervals or 6 to 12 ventricular event intervals as examples. At block 710, control circuit 206 may compare the representative ventricular event interval to the atrial rate interval corresponding to the atrial rate determined at block 704. Alternatively, control circuit 206 may determine the ventricular rate corresponding to the ventricular event interval for comparison to the atrial rate at block 710.

At block 710, control circuit 206 determines if the ventricular event intervals are tracking the atrial rate determined at block 704. For example, if the ventricular rate (or corresponding representative ventricular event interval) is within a predetermined threshold range of the atrial rate (or corresponding atrial rate interval) determined at block 704, control circuit 206 determines that the ventricular rate is tracking the atrial rate as expected. For instance, if the ventricular rate is within ±5 to 10 beats per minute of the determined atrial rate, atrial rate tracking may be determined at block 710. It is to be understood that comparing a ventricular rate to an atrial rate may be performed by control circuit 206 by comparing a determined ventricular rate interval to the atrial rate interval. Conversion of the determined ventricular and atrial rate intervals to a respective ventricular rate and atrial rate in beats per minute (or other units) is not necessary for determining if the ventricular rate matches the atrial rate.

The threshold range applied by control circuit 206 to the determined ventricular rate (or corresponding rate interval) may account for a decrease in the sinus rate that can occur when switching from an asynchronous ventricular pacing mode to a synchronous ventricular pacing mode. When the pacing mode is switched from an asynchronous to a synchronous ventricular pacing mode, an associated hemodynamic improvement due to improved AV synchrony, e.g., higher stroke volume on each ventricular systolic phase, may cause a decrease in sympathetic tone. The decrease in sympathetic tone may result in a normal decrease in the atrial sinus rate. Therefore, the threshold range applied to the ventricular rate may be defined as −20 bpm to +10 bpm relative to the determined atrial rate or −10 bpm to +5 bpm relative to the atrial rate, as examples. The threshold range may allow for a greater difference between the lower limit of the threshold range and the determined atrial rate than the difference between the upper limit of the threshold range and the atrial rate to account for a physiological decrease in the atrial sinus rate that can happen in response to improved AV synchrony upon switching to atrial synchronous ventricular pacing mode.

When the ventricular rate during the atrial synchronous pacing mode matches (within a threshold range) the atrial rate determined during the non-atrial tracking pacing mode, as determined at block 710, control circuit 206 may hold the A4 sensing threshold amplitude applied during the A3 and/or A4 windows at the currently set values at block 714. However, when the ventricular rate is determined to be outside a threshold range of the atrial rate, atrial event detector circuit 240 may not be reliably sensing atrial event signals on a beat-by-beat basis. Control circuit 206 may adjust one or more atrial event sensing control parameters at block 712 to improve atrial event sensing. The atrial event sensing control parameter(s) adjusted at block 712 may be selected by control circuit 206 based on whether the ventricular rate is greater than or less than the atrial rate and/or when during the ventricular cycle atrial event signals are being sensed.

In some instances, control circuit 206 may adjust the A4 sensing threshold amplitude during the A4 window and/or during the A3 window. When the ventricular rate is faster than the atrial rate, oversensing of atrial events may be occurring due to the A4 sensing threshold amplitude being too low. The early, high A4 sensing threshold amplitude applied during the A3 window and/or the later, low A4 sensing threshold amplitude applied during the A4 window may be increased at block 712. When the ventricular rate is less than the threshold range applied at block 710 by control circuit 206, atrial event signals may be undersensed by the atrial event detector circuit 240. Control circuit 206 may decrease the A4 sensing threshold amplitude applied during the A3 window and/or the A4 window. The A4 sensing threshold amplitude may be adjusted by a predetermined increment or decrement, e.g., 0.1, 0.2, 0.3, 0.4 or 0.5 $m/s^2$.

In some examples, the A4 sensing threshold applied during the A3 window is set to a nominal amplitude, e.g., 3.0 to 4.0 $m/s^2$, and the A4 sensing threshold applied during the A4 window (upon expiration of the A3 window) is set to a nominal amplitude, e.g., 1.2 to 1.6 $m/s^2$. If the ventricular rate is less than the atrial rate as determined by control circuit 206 at block 710, control circuit 206 may decrement the A4 sensing threshold amplitude that is applied during one or both of the A3 window and the A4 window at block 712.

In some examples, in order to determine whether to adjust the high A4 sensing threshold amplitude or the low A4 sensing threshold amplitude or both, control circuit 206 may assess what percentage of sensed atrial event signals occur during the A3 window and what percentage of sensed atrial event signals occur during the A4 window. If all or a relatively high percentage, e.g., 70% or more, of atrial event signals are sensed during the A4 window, control circuit 206 may increase the low A4 sensing threshold amplitude that is applied during the A4 window. If all or a relatively high percentage, e.g., 70% or more of atrial event signals occur during the A3 window, control circuit 206 may adjust the high A4 sensing threshold amplitude that is applied during the A3 window. When sensed atrial event signals are not sensed predominately in either the A3 window or during the A4 window, both the high A4 sensing threshold amplitude and the low A4 sensing threshold amplitude may be adjusted at block 712.

Control circuit 206 may return to block 708 to redetermine the ventricular rate after adjusting the A4 sensing threshold amplitude setting(s). After the adjustment(s) at block 712, the ventricular rate determined at block 708, using the techniques described above, may match the atrial rate previously determined at block 704, e.g., within the threshold range. If the ventricular rate matches the atrial rate, the A4 sensing control parameter(s) as adjusted may be maintained at the current setting(s) at block 714. If the ventricular rate does not match the previously determined atrial rate, further adjustments of atrial event sensing control parameters may be performed at block 712. In some examples, the A4 sensing threshold amplitude during the A3 window and/or the A4 window may continue to be adjusted (up or down) until the ventricular rate determined at block 708 matches the predetermined atrial rate. For instance, the A4 threshold amplitude during the A3 window and A4 window may be set to a nominal, starting value that is relatively high (e.g., 4.0 $m/s^2$ and 1.5 $m/s^2$, respectively, or higher) and be progressively decremented by control circuit 206 at block 712 until the ventricular rate determined at block 708 is found to match the determined atrial rate at block 710.

In some examples, control circuit 206 may return to block 702 to switch back to the non-atrial tracking ventricular pacing mode to redetermine the atrial rate when the ventricular rate does not match the atrial rate. For example, if a maximum number of adjustments or a maximum time limit since the atrial rate was determined is reached and the ventricular rate is not determined to match the determined atrial rate, control circuit 206 may return to block 702. Control circuit 206 may wait for a predetermined time interval, e.g., several minutes, one hour, one day or other time interval, before redetermining the atrial rate and remain in either the atrial synchronous or asynchronous ventricular pacing mode until the predetermined time interval has elapsed. In other examples, control circuit 206 may wait for a change in a physiological condition, e.g., a decrease in patient physical activity (which may be determined from a patient physical activity metric determined from the accelerometer signal) or a change in patient posture (which may also be determined from the accelerometer signal), before redetermining the atrial rate.

In other examples, in addition to or alternatively to adjusting the A4 sensing threshold amplitude, control circuit 206 may adjust the A3 window ending time at block 712. If greater than 20%, 30%, 40%, 50% or other threshold percentage of sensed atrial event signals are being sensed early in the A4 window, e.g., within the first 50 to 200 ms or within 100 ms after the A3 window ending time, and the ventricular rate is slower than the atrial rate (as determined at block 710), the A3 window ending time may be shortened by control circuit 206 at block 712. Atrial event signals occurring before the A3 window ending time but not fused with the A3 event signal, and therefore having a peak amplitude less than the high A4 sensing threshold amplitude, may be undersensed. Accordingly, control circuit 206 may shorten the A3 window, e.g., by 20 to 100 ms or about 50 ms as examples. The A3 window ending time may be adjusted one or more times, but not adjusted to less than a minimum A3 window ending time, until the ventricular rate determined at block 708 matches the atrial rate, as determined at block 710.

When pacemaker 14 is positioned in the RA for delivering ventricular pacing, for example as shown in FIG. 3, control circuit 206 may adjust a P-wave sensing control parameter at block 712 in response to the ventricular rate not matching the atrial rate determined from the motion signal during asynchronous ventricular pacing. The motion signal sensed by sensor 212 (FIG. 4) may be analyzed according to the techniques disclosed herein to verify that ventricular pacing pulses delivered at an AV pacing interval from sensed P-waves are tracking the determined atrial mechanical rate. In some instances, far field R-waves may interfere with P-wave sensing or P-wave undersensing could occur when the pacemaker is positioned in the right atrium for sensing atrial P-waves and delivering atrial synchronous ventricular pacing.

If control circuit 206 determines that the atrial synchronous ventricular paced rate is tracking (matches) the atrial rate that is determined from the motion signal during asynchronous ventricular pacing, P-wave sensing control parameters may be kept at the current parameters at block 714. However, if the ventricular paced rate during atrial synchronous ventricular pacing is outside a threshold range of the atrial rate determined from atrial events sensed from the motion signal during asynchronous ventricular pacing, P-wave sensing control parameters may require adjustment at block 712. Control parameters used to set the P-wave sensing threshold amplitude may be adjusted at block 712 and/or any time intervals, such as blanking or refractory periods, decay rates or intervals or the like used in controlling P-wave sensing from a sensed cardiac electrical signal, may be adjusted at block 712. P-wave sensing control parameters may be adjusted one or more times in response to determining that the atrial tracking ventricular pacing rate determined at block 708 is different than the atrial rate determined from the motion signal during non-atrial tracking ventricular pacing.

Figure 13:
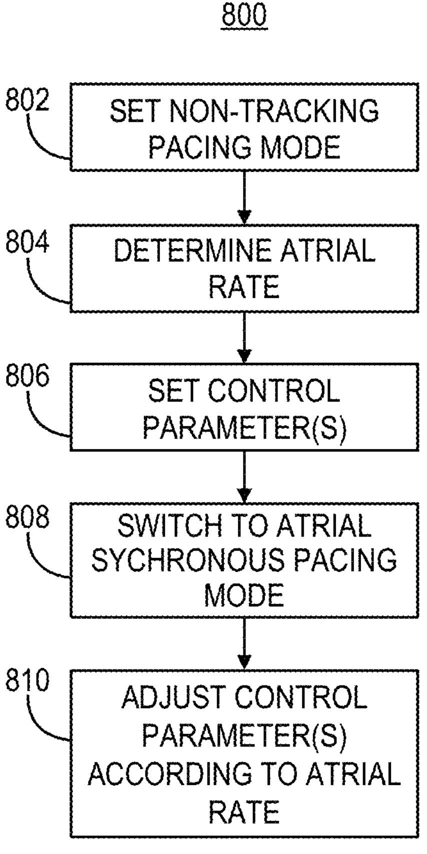
FIG. 13 is a flow chart of a method for determining atrial rate and setting one or more control parameters used by a pacemaker during an atrial synchronous ventricular pacing mode according to some examples.

FIG. 13 is a flow chart 800 of a method for determining atrial rate and setting one or more control parameters used by control circuit 206 in an atrial synchronous ventricular pacing mode according to some examples. At block 802, control circuit 206 sets the pacing mode to a non-atrial tracking ventricular pacing mode, e.g., a VDI pacing mode. At block 804, control circuit 206 determines the atrial rate using the techniques disclosed herein, e.g., as described above in conjunction with FIGS. 7-11.

At block 806, control circuit 206 sets one or more control parameters based on the determined atrial rate. The control parameter(s) set at block 806 can be used by control circuit 206 while operating in an atrial synchronized ventricular pacing mode and may therefore include control parameters used in sensing atrial events from the motion signal and, in some examples, may include control parameters used in delivering ventricular pacing pulses such as control parameters used in setting a rate smoothing pacing interval. The control parameter(s) may be programmed to a starting value by a user and adjusted from the starting value to an adjusted value based on the atrial rate at block 806. In other examples, the control parameter(s) may be set to a starting value during an auto set-up procedure as generally described in the above-incorporated U.S. Patent Application Publication No. 2020/0179707 (Splett, et al.) and in U.S. Patent Application Publication No. 2020/0179708 (Splett, et al.). Among the control parameters that may be set at block 806 based at least in part on the atrial rate determined at block 804 are an A3 window ending time, an A3 window ending time maximum and/or minimum limit, and/or a rate smoothing adjustment interval.

At block 806, control circuit 206 may set an A3 window ending time based on the atrial rate. For example, an A3 window ending time may be set to a percentage or portion of the atrial rate interval. In other examples, control circuit 206 may set a maximum A3 window ending time based on the atrial rate at block 806. Control circuit 206 may be configured to set the A3 window ending time to a starting value during a non-atrial tracking ventricular pacing mode according to an auto set-up procedure as described in the above-incorporated U.S. Patent Application Publication Nos. 2020/0179707 and 2020/0179708. Briefly, the A3 window ending time 422 shown in FIG. 6 may be initially set to a starting value based on an analysis of the motion signal by control circuit 206 during a non-atrial tracking ventricular pacing mode.

To illustrate, during a set-up procedure control circuit 206 may set a test threshold amplitude and determine the latest crossing time of the test threshold amplitude by the motion signal during a nominal A3 window. The nominal A3 window may begin after a post-ventricular blanking period, e.g., 500 to 700 ms or about 600 ms after a ventricular event, and extend until the next ventricular event, sensed or paced. In other examples, the nominal A3 window may be set to extend at least 70%, 80% or other portion of a median ventricular rate. Control circuit 206 may generate a histogram of latest test threshold crossing times during the nominal A3 window for storage in memory 210. The test threshold amplitude may be set to a nominal threshold amplitude, which may be between 0.8 to 1.0 $m/s^2$, or 0.9 $m/s^2$ as one example.

The frequency distribution of the histogram of latest test threshold crossing times is likely to be a bimodal distribution. The bimodal distribution is expected to include a first peak of latest amplitude threshold crossing times corresponding to true A3 event signals occurring relatively early during the nominal A3 window. The true A3 event signal is expected during every nominal A3 window because the A3 window is started in relation to a ventricular electrical event, sensed or paced, and the A3 event is a ventricular mechanical event that consistently follows the ventricular electrical event. The A4 event signal may or may not occur during the nominal A3 window because the atrial rate and the ventricular rate may be different and/or asynchronous. On at least some ventricular cycles, therefore, the A4 event signal may occur during the nominal A3 window and can appear as a relatively late amplitude threshold crossing. As such, the histogram of latest amplitude threshold crossing times may include a second peak of the bimodal distribution that corresponds to true A4 event signals occurring later in the nominal A3 window during ventricular cycles in which the asynchronous A4 event signals happen to occur in the nominal A3 window.

Control circuit 206 may set the A3 window ending time 422 (as shown in FIG. 6) based on the bimodal distribution by setting the A3 window ending time 422 to be between the two peaks of the bimodal distribution so that the A3 window includes A3 event signals with a high degree of likelihood without including A4 event signals that are not fused with the A3 event signals. For example, the A3 window ending time may be set to the earliest peak of the bimodal distribution latest amplitude threshold crossing times plus of offset, e.g., plus 50 to 200 ms. Other methods for establishing a starting value of the A3 window ending time are disclosed in the above-incorporated U.S. Patent Application Publication No. 2020/0179707 (Splett, et al.). In other examples, the A3 window may start 550 ms after the ventricular event and have an ending time 900 ms after the ventricular event.

After switching to an atrial synchronous ventricular pacing mode at block 808, e.g., a VDD pacing mode, control circuit 206 may be configured to adjust or update control parameters at block 810, e.g., based on the amplitude of the motion signal or based on a median ventricular cycle length determined by control circuit 206 during the atrial synchronous ventricular pacing mode. According to the techniques disclosed herein, the control parameters may be adjusted based in part on the determined atrial rate. For example, the A3 window ending time may be adjusted by control circuit 206 every N ventricular cycles to update the A3 window ending time to promote reliable atrial event signal sensing on a beat-by-beat basis. Techniques for adjusting the A3 window ending timing time during an atrial synchronous ventricular pacing mode are generally disclosed in the above-incorporated U.S. Patent Application Publication No. 2021/0236825 (Sheldon, et al.) and in U.S. Patent Application Publication No. 2021/0236826. Briefly, control circuit 206 may determine the time of a latest test threshold amplitude crossing of the motion sensor signal during the A3 window for one or more consecutive ventricular cycles. The test threshold amplitude may be set to a percentage, e.g., 75%, of the later, low A4 sensing threshold amplitude value that is applied during the A4 window and can be programmed or set during the auto set up procedures as generally described in the above-referenced U.S. Patent Application Publication No. 2020/0179707 (Splett, et al.) and U.S. Patent Application Publication No. 2020/0179708.

The median of the latest test threshold crossing times during the A3 window may be updated after every 3 to 12 ventricular cycles. The median time of the latest A3 threshold amplitude crossing may be determined as the $4^{th}$ shortest time out of 8 ventricular cycles in an illustrative example. The median of the latest test threshold crossing times may be used to set a target value of the A3 window ending time that is used to update the A3 window ending time after every 8 ventricular cycles. For example, the A3 window ending time may be adjusted from the current value of the A3 window ending time plus or minus an adjustment interval toward the target value.

Control circuit 206 may set the maximum A3 window ending time at block 806 based on the atrial rate. The maximum A3 window ending time limits how late the A3 window can end after a ventricular event (sensed or paced) when the A3 window ending time is being adjusted every N ventricular cycles. The maximum A3 window ending time may be set to be relatively shorter (earlier after a ventricular electrical event) when the atrial rate determined at block 804 is high and relatively longer (later after a ventricular electrical event) when the atrial rate is low.

For example, when the atrial rate is between 80 and 100 beats per minute, the maximum A3 window ending time 422 (shown in FIG. 6) may be set to be between 700 and 800 ms or to 750 or 775 ms as examples. When the atrial rate is less than 80 beats per minute, the maximum A3 window ending time 422 may be set longer, e.g., up to 900 to 1100 ms or to about 1000 ms as examples. The maximum A3 window ending time may be adjusted in a linear or step wise relationship with atrial rate such that the maximum A3 window ending time is shortened with shorter atrial rate intervals and increased with longer atrial rate intervals. The maximum A3 window ending time set based on the atrial rate at block 806 may be used to limit how long the A3 window is adjusted to at block 810 during atrial synchronous ventricular pacing and is therefore used in controlling atrial event sensing by atrial event detector circuit 240 during an atrial tracking pacing mode.

Additionally or alternatively, control circuit 206 may set a control parameter at block 806 by setting a rate smoothing increment based on the atrial rate. During an atrial synchronous ventricular pacing mode, control circuit 206 may determine a rate smoothing interval (RSI) used to set a ventricular pacing escape interval that controls the timing of a ventricular pacing pulse in the absence of an atrial event signal being sensed. The RSI is used to set a ventricular pacing escape interval that avoids an abrupt change in the ventricular pacing rate when an atrial event signal is not sensed. When a ventricular pacing pulse is delivered by pulse generator 202 or a ventricular sensed event signal is received from sensing circuit 204, control circuit 206 may start the ventricular pacing escape interval set to the RSI. If the ventricular pacing escape interval expires before an atrial event signal is sensed, pulse generator 202 may deliver a ventricular pacing pulse to maintain ventricular rate support without an abrupt change in ventricular rate.

The RSI may be used to control the ventricular pacing rate to gradually slow to a lower pacing rate. A user may program the lower pacing rate to provide pacing at a minimum ventricular pacing rate, e.g., of 40, 50 or 60 beats per minute, when atrial events are not being sensed, which could occur during atrial fibrillation for instance. When atrial event signals are being sensed beat to beat, the paced ventricular rate that is tracking the sensed atrial event signals is higher than the programmed lower rate. In an illustrative example, the programmed lower rate may be 40 beats per minute (a lower rate interval of 1.5 seconds), but the actual ventricular paced rate during the atrial synchronous ventricular pacing may be 70 beats per minute. If an atrial event signal is not sensed during a pacing escape interval set to the lower rate interval (LRI) of 1.5 seconds in this example, the ventricular rate could drop from 70 beats per minute to 40 beats per minute in one ventricular cycle. Instead, control circuit 206 sets an RSI based on the actual ventricular rate of 70 beats per minute. The RSI may be set based on an actual ventricular rate interval plus a smoothing interval. In this way, control circuit 206 can gradually adjust the ventricular paced rate from 70 to 40 beats per minute when atrial event sensing is lost.

In some examples, control circuit 206 determines a rate smoothing base interval (RSBI) from the most recent paced ventricular cycle length (VCL). The RSBI may be initialized to the programmed LRI. The RSBI may be compared to the next paced VCL determined by control circuit 206 as the time interval between two consecutive pacing pulses. If the RSBI is greater than the next paced VCL, it is decreased by an adjustment interval, e.g., by 8 to 20 ms. If the RSBI is less than the next paced VCL, it is increased by the adjustment interval. If the RSBI is equal to (or within an adjustment interval) of the most recent paced VCL, it is not adjusted and remains at its current value. In this way, control circuit 206 may update the RSBI on each paced VCL to track the actual paced ventricular rate on a beat by beat basis. The RSBI may be adjusted up or down by a relatively small adjustment interval, e.g., 8 to 20 ms, based on the actual VCL(s), so that the RSBI trends toward and closely follows the actual VCL.

The RSI is determined by control circuit 206 as the RSBI plus a smoothing increment. The smoothing increment may be set at block 806 by control circuit 206 based on the atrial rate. The RSI may be updated at block 810 each time the RSBI is updated by adding the smoothing increment to the RSBI. In other examples, the RSI can be updated at block 810 every N ventricular cycles, e.g., every 3 to 20 ventricular cycles or every 8 ventricular cycles, by adding the smoothing increment determined at block 806 based on atrial rate to the current value of the RSBI. By adding the smoothing increment to the RSBI and setting the ventricular pacing escape interval to the RSI, the actual paced ventricular rate is gradually slowed to the programmed lower rate when atrial event signal sensing is lost. When atrial event signal sensing is intermittent, ventricular pacing pulses at the RSI maintain a relatively smooth ventricular rate, avoiding abrupt changes in ventricular rate on ventricular cycles during which an atrial event signal is not sensed before expiration of the ventricular pacing escape interval.

The smoothing increment added to the RSBI to obtain the RSI may be set to 10 ms, 25 ms, 50 ms, 75 ms, 100 ms, 150 ms, 200 ms, 250 ms or any other time interval, which may be selected at block 806 by control circuit 206 based on the atrial rate determined at block 804 of FIG. 13. A shorter smoothing increment may be used during relatively higher atrial rates and a longer smoothing increment may be used during relatively lower atrial rates. The smoothing increment may be set as a percentage of the atrial rate, such as 8%, 10%, 12%, 15%, or 20% as examples. In other examples, different fixed smoothing increments may be set for different atrial rate ranges. For example when the atrial rate is less than or equal to 80 beats per minute, the smoothing increment may be set to 100 ms. When the atrial rate is greater than 80 beats per minute, the smoothing increment may be set to 50 ms. It is to be understood that more than two fixed predetermined increments may be stored in memory 210, e.g., in a look-up table, in conjunction with a corresponding atrial rate range, to be used by control circuit 206 for adjusting the RSI at block 810, e.g., by adding the smoothing increment to a determined RSBI.

While the examples described here relating to setting a smoothing increment and adjusting an RSI refer to paced VCLs, it is to be understood that control circuit 206 may set an RSI in response to a sensed ventricular event signal and in some cases set an RSI based at least in part on a ventricular event interval that either starts or ends with a ventricular sensed event signal. Various examples of setting and adjusting an RSI that may utilize a smoothing increment set based on an atrial rate determined using the techniques disclosed herein are generally described in provisional U.S. Patent Application No. 63/173,523 (Sheldon, et al.) and corresponding U.S. patent application Ser. No. 17/697,795 published as U.S. Patent Application Publication No. 2022/0323768 (Sheldon, et al.), incorporated herein by reference in its entirety.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising:

a motion sensor configured to sense a motion signal;

a pulse generator configured to generate ventricular pacing pulses; and a control circuit configured to:

control the pulse generator to generate pacing pulses in a non-atrial tracking ventricular pacing mode;

sense atrial event signals from the motion signal sensed by the motion sensor during the non-atrial tracking ventricular pacing mode;

determine atrial event intervals from the sensed atrial event signals;

determine a frequency distribution of the determined atrial event intervals;

determine an atrial rate interval based on the frequency distribution of the atrial event intervals;

set at least one control parameter based on the determined atrial rate interval, the at least one control parameter being used by the control circuit during an atrial synchronous ventricular pacing mode; and control the pulse generator to generate ventricular pacing pulses according to the atrial synchronous ventricular pacing mode.

2. The medical device of claim 1, wherein the control circuit is further configured to determine the atrial rate interval based on the frequency distribution of the atrial event intervals by:

determining a harmonic relationship between the atrial event intervals based on the frequency distribution; and determining the atrial rate interval based on the harmonic relationship of the determined atrial event intervals.

3. The medical device of claim 2, wherein the control circuit is further configured to:

determine the harmonic relationship by determining a first harmonic relationship of the atrial event intervals and a second harmonic relationship of the atrial event intervals;

select a best fit harmonic relationship to the atrial event intervals from among the first harmonic relationship and the second harmonic relationship;

determine a fundamental period of the selected best fit harmonic relationship; and determine the atrial rate interval based on the fundamental period.

4. The medical device of claim 3, wherein the control circuit is further configured to select the best fit harmonic relationship by at least one of:

determining a goodness of fit measurement of each of the first harmonic relationship and the second harmonic relationship and selecting the best fit harmonic relationship based on the goodness of fit measurement; and determining a systolic event time interval from the motion signal and selecting the best fit harmonic relationship based on the systolic event time interval.

5. The medical device of claim 3, wherein the control circuit is further configured to:

identify a first peak of the frequency distribution of the atrial event intervals;

determine a representative atrial event interval associated with the first peak of the frequency distribution;

determine the first harmonic relationship of the atrial event intervals by setting the representative atrial event interval equal to a first harmonic; and determine the second harmonic relationship of the atrial event intervals by setting the representative atrial event interval associated with the first peak of the frequency distribution equal to a second harmonic.

6. The medical device of claim 1, wherein the control circuit is further configured to:

set a ventricular event window ending time;

set an atrial event sensing threshold amplitude by setting a first threshold amplitude applied to the motion signal before the ventricular event window ending time and setting a second threshold amplitude lower than the first threshold amplitude, the second threshold amplitude applied to the motion signal after the ventricular event window ending time; and sense atrial event signals from the motion signal sensed by the motion sensor during the non-atrial tracking ventricular pacing mode in response to the motion signal crossing one of the first threshold amplitude or the second threshold amplitude.

7. The medical device of claim 1, wherein:

the control circuit is further configured to:

set the at least one control parameter by setting an atrial event sensing control parameter; and detect an atrial event signal from the motion signal based on the atrial event sensing control parameter during the atrial synchronous ventricular pacing mode;

set an atrioventricular pacing interval in response to detecting the atrial event signal from the motion signal during the atrial synchronous ventricular pacing mode; and determine that the atrioventricular pacing interval expires; and the pulse generator is configured to generate a ventricular pacing pulse in response to the atrioventricular pacing interval expiring.

8. The medical device of claim 1, wherein the control circuit is further configured to:

set the at least one control parameter based on the determined atrial rate interval by setting a rate smoothing increment based on the atrial rate interval;

set a rate smoothing interval using the rate smoothing increment;

identify a ventricular event during the atrial synchronous ventricular pacing mode; and start a ventricular pacing escape interval set to the rate smoothing interval in response to identifying the ventricular event.

9. The medical device of claim 1, wherein the control circuit is further configured to set the at least one control parameter based on the determined atrial rate interval by:

determining a ventricular rate interval during the atrial synchronous ventricular pacing mode;

determining that the ventricular rate interval is different than the atrial rate interval; and setting the at least one control parameter by adjusting an atrial event sensing control parameter in response to the ventricular rate interval being different than the atrial rate interval.

10. The medical device of claim 9, wherein the control circuit is further configured to:

set a ventricular event window ending time;

set an atrial event sensing threshold amplitude by setting a first threshold amplitude applied to the motion signal before the ventricular event window ending time and setting a second threshold amplitude lower than the first threshold amplitude, the second threshold amplitude applied to the motion signal after the ventricular event window ending time; and set the atrial event sensing control parameter in response to the ventricular rate interval being different than the atrial rate interval by adjusting at least one of the ventricular event window ending time, the first threshold amplitude and the second threshold amplitude.

11. The medical device of claim 1, further comprising:

a housing enclosing the motion sensor, the pulse generator and the control circuit; and a pair of electrodes on the housing and coupled to the pulse generator for delivering the ventricular pacing pulses.

12. A method comprising:

sensing a motion signal;

generating pacing pulses in a non-atrial tracking ventricular pacing mode;

sensing atrial event signals from the motion signal during the non-atrial tracking ventricular pacing mode;

determining atrial event intervals from the sensed atrial event signals;

determining a frequency distribution of the determined atrial event intervals;

determining an atrial rate interval based on the frequency distribution of the atrial event intervals;

setting at least one control parameter based on the determined atrial rate interval, the at least one control parameter being used during an atrial synchronous ventricular pacing mode; and generating ventricular pacing pulses according to the atrial synchronous ventricular pacing mode.

13. The method of claim 12, further comprising determining the atrial rate interval based on the frequency distribution of the atrial event intervals by:

determining a harmonic relationship between the atrial event intervals based on the frequency distribution; and determining the atrial rate interval based on the harmonic relationship of the determined atrial event intervals.

14. The method of claim 13, further comprising:

determining the harmonic relationship by determining a first harmonic relationship of the atrial event intervals and a second harmonic relationship of the atrial event intervals;

selecting a best fit harmonic relationship to the atrial event intervals from among the first harmonic relationship and the second harmonic relationship;

determining a fundamental period of the selected best fit harmonic relationship; and determining the atrial rate interval based on the fundamental period.

15. The medical device of claim 14, wherein at least one electrode of the pair of electrodes is a tissue piercing electrode configured for delivering the ventricular pacing pulses.

16. The method of claim 14, wherein selecting the best fit harmonic relationship comprises at least one of:

determining a goodness of fit measurement of each of the first harmonic relationship and the second harmonic relationship and selecting the best fit harmonic relationship based on the goodness of fit measurement; and determining a systolic event time interval from the motion signal and selecting the best fit harmonic relationship based on the systolic event time interval.

17. The method of claim 14, further comprising:

identifying a first peak of the frequency distribution of the atrial event intervals;

determining a representative atrial event interval associated with the first peak of the frequency distribution;

determining the first harmonic relationship of the atrial event intervals by setting the representative atrial event interval equal to a first harmonic; and determining the second harmonic relationship of the atrial event intervals by setting the representative atrial event interval associated with the first peak of the frequency distribution equal to a second harmonic.

18. The method of claim 12, further comprising:

setting a ventricular event window ending time;

setting an atrial event sensing threshold amplitude by setting a first threshold amplitude applied to the motion signal before the ventricular event window ending time and setting a second threshold amplitude lower than the first threshold amplitude, the second threshold amplitude applied to the motion signal after the ventricular event window ending time; and sensing atrial event signals from the motion signal sensed by the motion sensor during the non-atrial tracking ventricular pacing mode in response to the motion signal crossing one of the first threshold amplitude or the second threshold amplitude.

19. The method of claim 12, further comprising:

setting the at least one control parameter by setting an atrial event sensing control parameter;

detecting an atrial event signal from the motion signal based on the atrial event sensing control parameter during the atrial synchronous ventricular pacing mode;

setting an atrioventricular pacing interval in response to detecting the atrial event signal from the motion signal during the atrial synchronous ventricular pacing mode;

determining that the atrioventricular pacing interval expires; and generating a ventricular pacing pulse in response to the atrioventricular pacing interval expiring.

20. The method of claim 12, further comprising:

setting the at least one control parameter by setting a rate smoothing increment based on the atrial rate interval;

setting a rate smoothing interval using the rate smoothing increment;

identifying a ventricular event during the atrial synchronous ventricular pacing mode; and starting a ventricular pacing escape interval set to the rate smoothing interval in response to identifying the ventricular event.

21. The method of claim 12, further comprising setting the at least one control parameter based on the determined atrial rate interval by:

determining a ventricular rate during the atrial synchronous ventricular pacing mode;

determining that the ventricular rate interval is different than the atrial rate interval; and setting the at least one control parameter by adjusting an atrial event sensing control parameter in response to the ventricular rate interval being different than the atrial rate interval.

22. The method of claim 21, further comprising:

setting a ventricular event window ending time;

setting an atrial event sensing threshold amplitude by setting a first threshold amplitude applied to the motion signal before the ventricular event window ending time and setting a second threshold amplitude lower than the first threshold amplitude, the second threshold amplitude applied to the motion signal after the ventricular event window ending time; and adjusting the atrial event sensing control parameter in response to the ventricular rate being different than the atrial rate by adjusting at least one of the ventricular event window ending time, the first threshold amplitude and the second threshold amplitude.

23. A non-transitory, computer-readable storage medium comprising a set of instructions which, when executed by a control circuit of a medical device, cause the medical device to:

sense a motion signal;

generate pacing pulses in a non-atrial tracking ventricular pacing mode;

detect atrial event signals from the motion signal during the non-atrial tracking ventricular pacing mode;

determine atrial event intervals from the detected atrial event signals;

determine a frequency distribution of the determined atrial event intervals;

determine an atrial rate interval based on the frequency distribution of the detected atrial event intervals;

set at least one control parameter based on the determined atrial rate interval, the at least one control parameter being used during an atrial synchronous ventricular pacing mode; and generate ventricular pacing pulses according to the atrial synchronous ventricular pacing mode.

* * * * *